US009068007B2

(12) United States Patent
Zhong

(10) Patent No.: US 9,068,007 B2
(45) Date of Patent: Jun. 30, 2015

(54) METHODS AND COMPOSITIONS FOR CHLAMYDIAL ANTIGENS FOR DIAGNOSIS AND TREATMENT OF CHLAMYDIAL INFECTION AND DISEASE

(75) Inventor: Guangming Zhong, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 411 days.

(21) Appl. No.: 13/123,407

(22) PCT Filed: Oct. 9, 2009

(86) PCT No.: PCT/US2009/005541
§ 371 (c)(1),
(2), (4) Date: Jul. 11, 2011

(87) PCT Pub. No.: WO2010/042206
PCT Pub. Date: Apr. 15, 2010

(65) Prior Publication Data
US 2011/0256094 A1    Oct. 20, 2011

Related U.S. Application Data

(60) Provisional application No. 61/104,017, filed on Oct. 9, 2008.

(51) Int. Cl.
*G01N 33/53* (2006.01)
*A61K 39/118* (2006.01)
*A61K 49/00* (2006.01)
*C07K 14/295* (2006.01)
*G01N 33/569* (2006.01)
*A61K 39/00* (2006.01)

(52) U.S. Cl.
CPC ............. *C07K 14/295* (2013.01); *A61K 39/00* (2013.01); *G01N 33/56927* (2013.01)

(58) Field of Classification Search
USPC ................. 424/9.1, 9.2, 130.1, 139.1, 164.1, 424/184.1, 185.1, 234.1, 263.1; 435/4, 7.1, 435/7.2
See application file for complete search history.

(56) References Cited

U.S. PATENT DOCUMENTS

| | | |
|---|---|---|
| 6,432,916 B1 | 8/2002 | Probst et al. |
| 6,448,234 B1 | 9/2002 | Fling |
| 6,565,856 B1 | 5/2003 | Skeiky et al. |
| 6,746,676 B1 | 6/2004 | Rockey et al. |
| 6,822,071 B1 | 11/2004 | Stephens et al. |
| 6,919,187 B2 | 7/2005 | Bhatia et al. |
| 7,892,567 B2 | 2/2011 | Arulanandam et al. |
| 8,092,812 B2 | 1/2012 | Arulanandam et al. |
| 8,440,208 B2 | 5/2013 | Zhong |
| 2005/0106162 A1 | 5/2005 | Grandi et al. |
| 2005/0266016 A1 | 12/2005 | Stephens et al. |
| 2006/0034871 A1* | 2/2006 | Grandi et al. .............. 424/263.1 |
| 2007/0003568 A1 | 1/2007 | Dautry-Varsat et al. |
| 2009/0098165 A1 | 4/2009 | Arulanandam et al. |
| 2009/0304722 A1 | 12/2009 | Theisen et al. |
| 2010/0119549 A1 | 5/2010 | Zhong et al. |
| 2011/0123491 A1 | 5/2011 | Arulanandam et al. |
| 2011/0256094 A1 | 10/2011 | Zhong |

FOREIGN PATENT DOCUMENTS

| | | | |
|---|---|---|---|
| EP | 0 499 681 | 8/1992 | |
| JP | H10503922 A | 4/1998 | |
| JP | 2001286295 A | 10/2001 | |
| JP | 2005511076 A | 4/2005 | |
| WO | WO 95/28487 | 10/1995 | |
| WO | WO 02/079244 | 10/2002 | |
| WO | WO 02/082091 | 10/2002 | |
| WO | WO 03/049762 A2 | 6/2003 | |
| WO | WO2005002619 | * 1/2005 | ........... A61K 39/118 |
| WO | WO 2006/045308 A2 | 5/2006 | |
| WO | WO 2006/050571 A1 | 5/2006 | |
| WO | WO2007030879 | * 3/2007 | ............... C12Q 1/04 |
| WO | WO 2007/110700 A2 | 10/2007 | |
| WO | WO 2008/134085 | 11/2008 | |
| WO | WO 2010/042206 | 4/2010 | |

OTHER PUBLICATIONS

Dictionary of Microbiology and Molecular Biology, second Edition, eds. Singleton &Saninsbury, John Wiley & Sons, New York, p. 452, 1996.*

Arulanandam et al. "Intranasal Interleukin-12 is a Powerful Adjuvant for Protective Mucosal Immunity" *The Journal of Infectious Diseases* 180:940-949 (1999).

Balakrishnan et al. "Metalloprotease Inhibitors GM6001 and TAPI-0 Inhibit the Obligate Intracellular Human Pathogen *Chlamydia trachomatis* by Targeting Peptide Deformylase of the Bacterium" *The Journal of Biological Chemistry* 281(24):16691-16699 (2006).

Belland et al. "Genomic Transcriptional Profiling of the Developmental Cycle of *Chlamydia trachomatis*" *PNAS* 100(14):8478-8483 (2003).

Brunham and Rey-Ladino. "Immunology of *Chlamydia* Infection: Implications for a *Chlamydia trachomatis* Vaccine" *Nature Reviews / Immunology* 5:149-161 (2005).

Buchanan et al. "IL-12 Enhances Antibody Responses to T-Independent Polysaccharide Vaccines in the Absence of T and NK Cells" *Journal of Immunology* 161:5525-5533 (1998).

(Continued)

*Primary Examiner* — Rodney P Swartz
(74) *Attorney, Agent, or Firm* — Myers Bigel Sibley & Sajovec, P.A.

(57) ABSTRACT

Disclosed are isolated *Chlamydia trachomatis* proteins, methods of fusion protein and associated antibody production, and methods of using isolated proteins and antibodies in diagnosis and detection. Also disclosed are compositions comprising isolated proteins, wherein the compositions can further comprising pharmaceutically acceptable carriers, an adjuvant and/or an immunostimulant, and methods using the pharmaceutical compositions for treating or preventing an infection by *Chlamydia* in a subject. The compositions may also comprise a protein or immunogenic fragment of a pathogenic organism other than *Chlamydia trachomatis*.

18 Claims, No Drawings

(56) References Cited

OTHER PUBLICATIONS

Chaganty et al. "Heat Denatured Enzymatically Inactive Recombinant Chlamydial Protease-Like Activity Factor Induces Robust Protective Immunity Against Genital Chlamydial Challenge" *Vaccine* 28(11):2323-2329 (2009).

Cong et al. "Intranasal Immunization with Chlamydial Protease-Like Activity Factor and CpG Deoxynucleotides Enhances Protective Immunity Against Genital *Chlamydia muridarum* Infection" *Vaccine* 25(19):3773-3780 (2007).

Dong et al. "Cleavage-Dependent Activation of a *Chlamydia*-Secreted Protease" *Molecular Microbiology* 52(5):1487-1494 (2004).

Dong et al. "Cleavage of Host Keratin 8 by a *Chlamydia*-Secreted Protease" *Infection and Immunity* 72(7):3863-3868 (2004).

Dong et al. "Degradation of the Proapoptotic Proteins Bik, Puma, and Bim with Bcl-2 Domain 3 Homology in *Chlamydia trachomatis*-Infected Cells" *Infection and Immunity* 73(3):1861-1864 (2005).

Dong et al. "Intramolecular Dimerization is Required for the *Chlamydia*-Secreted Protease CPAF to Degrade Host Transcriptional Factors" *Infection and Immunity* 72(7):3869-3875 (2004).

Dong et al. "Localization of the Hypothetical Protein Cpn0797 in the Cytoplasm of *Chlamydia pneumoniae*-Infected Host Cells" *Infection and Immunity* 74(11):6479-6486 (2006).

Dong et al. "Production of a Proteolytically Active Protein, Chlamydial Protease/Proteasome-Like Activity Factor, by Five Different *Chlamydia* Species" *Infection and Immunity* 73(3):1868-1872 (2005).

Dong et al. Author's Correction to "Production of Proteolytically Active Protein, Chlamydial Protease/Protesome-Like Activity Factor, by Five Different *Chlamydia* Species" *Infection and Immunity* 73(7):4460 (2005).

Chen et al. "The Hypothetical Protein CT813 is Localized in *Chlamydia trachomatis* Inclusion Membrane and is Immunogenic in Women Urogenitally Infected with *C. trachomatis*" *Infection and Immunity* 74(8):4826-4840 (2006).

Crane et al. "*Chlamydia trachomatis* Polymorphic Membrane Protein D is a Species-Common Pan-Neutralizing Antigen" *PNAS* 103:1894-1899 (2006).

Fan et al. "*Chlamydia pneumoniae* Secretion of a Protease-Like Activity Factor for Degrading Host Cell Transcription Factors is Required for Major Histocompatibility Complex Antigen Expression" *Infection and Immunity* 70(1):345-349 (2002).

Fan et al. "Inhibition of Apoptosis in *Chlamydia*-Infected Cells: Blockade of Mitochondrial Cytochrome c Release and Caspase Activation" *J Exp Med* 187(4):487-496 (1998).

Flores et al. "Characterization of the Hypothetical Protein Cpn1027, a Newly Identified Inclusion Membrane Protein Unique to *Chlamydia pneumoniae*" *Microbiology* 153:777-786 (2007).

Fong et al. "Collaborative Multidisciplinary Workshop Report: What Questions Regarding the Role of *Chlamydia pneumoniae* in Atherosclerosis and Cardiovascular Disease Need to be Addressed Utilizing Animal Models?" *The Journal of Infectious Diseases* 181(Suppl 3):S519-S520 (2000).

GenBank Accession No. AAC68456. Hypothetical Protein (*Chlamydia trachomatis*), May 20, 1998 (1 page).

GenBank Accession No. NP_220380. Predicted Protease Containing IRBP and DHR Domains (*Chlamydia trachomatis*), Sep. 10, 2001 (2 pages).

Gervassi et al. "Human CD8$^+$ T Cells Recognize the 60-kDa Cysteine-Rich Outer Membrane Protein from *Chlamydia trachomatis*" *J. Immunol* 173:6905-6913 (2004).

Greene and Zhong. "Inhibition of Host Cell Cytokinesis by *Chlamydia trachomatis* Infection" *Journal of Infection* 47:45-51 (2003).

Greene et al. "*Chlamydia*-Infected Cells Continue to Undergo Mitosis and Resist Induction of Apoptosis" *Infection and Immunity* 72(1):451-460 (2004).

Greenspan and Di Cera. "Defining Epitopes: It's Not as Easy as it Seems" *Nature Biotechnology* 17:936-937 (1999).

Hu et al. "The Atherogenic Effects of *Chlamydia* are Dependent on Serum Cholesterol and Specific to *Chlamydia pneumoniae*" *The Journal of Clinical Investigation* 103(5):747-753 (1999).

International Search Report and Written Opinion for International Application No. PCT/US2008/005616, mailed Jul. 15, 2008 (11 pages).

Jupelli et al. "Endogenous IFN-γ Production is Induced and Required for Protective Immunity Against Pulmonary Chlamydial Infection in Neonatal Mice" *The Journal of Immunology* 180:4148-4155 (2008).

Jupelli et al. "The Contribution of Interleukin-12/Interferon-γ Axis in Protection Against Neonatal Pulmonary *Chlamydia muridarum* Challenge" *Journal of Interferon & Cytokine Research* 30(6):407-415 (2010).

Li et al. "Antigen-Specific CD4$^+$ T Cells Produce Sufficient IFN-γ to Mediate Robust Protective Immunity Against Genital *Chlamydia muridarum* Infection" *The Journal of Immunology* 180:3375-3382 (2008).

Li et al. "Immunization with a Combination of Integral Chlamydial Antigens and a Defined Secreted Protein Induces Robust Immunity Against Genital Chlamydial Challenge" *Infection and Immunity* 78(9):3942-3949 (2010).

Li et al. "Induction of Cross-Serovar Protection Against Genital Chlamydial Infection by a Targeted Multisubunit Vaccination Approach" *Clinical and Vaccine Immunology* 14(12):1537-1544 (2007).

Liu et al. "*Chlamydia pneumoniae* Infection Significantly Exacerbates Aortic Atherosclerosis in an LDLR-/- Mouse Model within Six Months" *Molecular and Cellular Biochemistry* 215:123-128 (2000).

Lu et al. "Interleukin-12 is Required for Chlamydial Antigen-Pulsed Dendritic Cells to Induce Protection Against Live *Chlamydia trachomatis* Infection" *Infection and Immunity* 67(4):1763-1769 (1999).

Luo et al. "Characterization of Hypothetical Proteins Cpn0146, 0147, 0284 & 0285 that are Predicted to be in the *Chlamydia pneumoniae* Inclusion Membrane" *BMC Microbiology* 7(38):12 pages (2007).

Luo et al. "Hypothetical Protein Cpn0308 is Localized in the *Chlamydia pneumoniae* Inclusion Membrane" *Infection and Immunity* 75(1):497-503 (2007).

Luo et al. "Localization of the Hypothetical Protein Cpn0585 in the Inclusion Membrane of *Chlamydia pneumoniae*-Infected Cells" *Microb Pathog* 42(2-3):111-116 (2007).

Murphey et al. "The Protective Efficacy of Chlamydial Protease-Like Activity Factor Vaccination is Dependent Upon CD4$^+$ T Cells" *Cell Immunol.* 242(2):110-117 (2006).

Murphy et al. Chapter 3: "Antigen Recognition by B-Cell and T-Cell Receptors" in *Immunology*, 7$^{th}$ Edition, pp. 111-143, Garland Science, New York (2008).

Murphy et al. "Somatic Antigens of *Haemophillus influenzae* as Vaccine Components" *Pediatr Infect Dis* 8:S66-S68 (1989).

Murthy et al. "A Limited Role for Antibody in Protective Immunity Induced by rCPAF and CpG Vaccination Against Primary Genital *Chlamydia muridarum* Challenge" *FEMS Immunol Med Microbiol* 55:271-279 (2009).

Murthy et al. "*Chlamydia trachomatis* Pulmonary Infection Induces Greater Inflammatory Pathology in Immunoglobulin a Deficient Mice" *Cellular Immunology* 230:56-64 (2004).

Murthy et al. "Chlamydial Protease-Like Activity Factor Induces Protective Immunity Against Genital Chlamydial Infection in Transgenic Mice That Express the Human HLA-DR4 Allele" *Infection and Immunity* 74(12):6722-6729 (2006).

Murthy et al. "Chlamydial Protease-Like Activity Factor—Insights into Immunity and Vaccine Development" *J Reprod Immunol* 83(1-2):179-184 (2009).

Murthy et al. "Intranasal Vaccination with a Secreted Chlamydial Protein Enhances Resolution of Genital *Chlamydia muridarum* Infection, Protects Against Oviduct Pathology, and is Highly Dependent Upon Endogenous Gamma Interferon Production" *Infection and Immunity* 75(2):666-676 (2007).

Murthy et al. "Vaccination with the Defined Chlamydial Secreted Protein CPAF Induces Robust Protection Against Female Infertility Following Repeated Genital Chlamydial Challenge" *Vaccine* 29:2519-2522 (2011).

(56) References Cited

OTHER PUBLICATIONS

Pirbhai et al. "The Secreted Protease Factor CPAF is Responsible for Degrading Pro-Apoptotic BH3-Only Proteins in *Chlamydia trachomatis*-Infected Cells" *The Journal of Biological Chemistry* 281(42):31495-31501 (2006).

Sharma et al. "Human Antibody Responses to a Chlamydia-Secreted Protease Factor" *Infection and Immunity* 72(12):7164-7171 (2004).

Sharma et al. "Inhibition of Proteolytic Activity of a Chlamydial Proteasome/Protease-Like Activity Factor by Antibodies from Humans Infected with *Chlamydia trachomatis*" *Infection and Immunity* 73(7):4414-4419 (2005).

Sharma et al. "Profiling of Human Antibody Responses to *Chlamydia trachomatis* Urogenital Tract Infection Using Microplates Arrayed with 156 Chlamydial Fusion Proteins" *Infection and Immunity* 74(3):1490-1499 (2006).

Starnback et al. "An Inclusion Membrane Protein from *Chlamydia trachomatis* Enters the MHC Class I Pathway and Stimulates a $CD8^+$ T Cell Response" *J. Immunol* 171:4742-4749 (2003).

Su et al. "Activation of Raf/MEK/ERK/cPLA2 Signaling Pathway is Essential for Chlamydial Acquisition of Host Glycerophospholipids" *The Journal of Biological Chemistry* 279(10):9409-9416 (2004).

Toye et al. "Immunologic Characterization of a Cloned Fragment Containing the Species-Specific Epitope from the Major Outer Membrane Protein of *Chlamydia trachomatis*" *Infection and Immunity* 58(12):3909-3913 (1990).

Wang et al. "Effect of Host Fatty Acid-Binding Protein and Fatty Acid Uptake on Growth of *Chlamydia trachomatis* L2" *Microbiology* 153:1935-1939 (2007).

Wang et al. "Infection of Myocytes with Chlamydiae" *Microbiology* 148:3955-3959 (2002).

Wolf et al. "*Chlamydia pneumoniae* Major Outer Membrane Protein is a Surface-Exposed Antigen that Elicits Antibodies Primarily Directed Against Conformation-Dependent Determinants" *Infection and Immunity* 69(5):3082-3091 (2001).

Xiao et al. "*Chlamydia trachomatis* Infection Inhibits Both Bax and Bak Activation Induced by Staurosporine" *Infection and Immunity* 72(9):5470-5474 (2004).

Xiao et al. "NF-κβ Activation is not Required for *Chlamydia trachomatis* Inhibition of Host Epithelial Cell Apoptosis" *The Journal of Immunology* 174:1701-1708 (2005).

Yamanaka and Faden. "Antibody Response to Outer Membrane Protein of Nontypeable *Haemophilus influenzae* in Otitis-Prone Children" *J Pediatrics* 122(2):212-218 (1993).

Yi et al. "Continuous B-Cell Epitopes in *Chlamydia trachomatis* Heat Shock Protein 60" *Infection and Immunity* 61(3):1117-1120 (1993).

Zhang et al. "A MyD88-Dependent Early IL-17 Production Protects Mice Against Airway Infection with the Obligate Intracellular Pathogen *Chlamydia muridarum*" *J Immunol* 183(2):1291-1300 (2009).

Zhang et al. "Immunity to *Chlamydia trachomatis* Mouse Pneumonitis Induced by Vaccination with Live Organisms Correlates with Early Granulocyte-Macrophage Colony-Stimulating Factor and Interleukin-12 Production and with Dendritic Cell-Like Maturation" *Infection and Immunity* 67(4):1606-1613 (1999).

Zhong and Brunham. "Antibody Responses to the Chlamydial Heat Shock Proteins hsp60 and hsp70 are H-2 Linked" *Infection and Immunity* 60(8):3143-3149 (1992).

Zhong and Brunham. "Antigenic Analysis of the Chlamydial 75-Kilodalton Protein" *Infection and Immunity* 60(3):1221-1224 (1992).

Zhong and Brunham. "Antigenic Determinants of the Chlamydial Major Outer Membrane Protein Resolved at a Single Amino Acid Level" *Infection and Immunity* 59(3):1141-1147 (1991).

Zhong and Brunham. "Immunoaccessible Peptide Sequences of the Outer Membrane Protein from *Chlamydia trachomatis* Serovar C" *Infection and Immunity* 58(10):3438-3441 (1990).

Zhong et al. "Antibody Recognition of a Neutralization Epitope on the Major Outer Membrane Protein of *Chlamydia trachomatis*" *Infection and Immunity* 62(5):1576-1583 (1994).

Zhong et al. "*Chlamydia* Inhibits Interferon γ-Inducible Major Histocompatibility Complex Class II Expression by Degradation of Upstream Stimulatory Factor 1" *J. Exp. Med.* 189(12):1931-1937 (1999).

Zhong et al. "Conformational Mimicry of a Chlamydial Neutralization Epitope on Filamentous Phage" *The Journal of Biological Chemistry* 269(39):24183-24188 (1994).

Zhong et al. "Degradation of Transcriptional Factor RFX5 During the Inhibition of Both Constitutive and Interferon γ-Inducible Major Histocompatibility Complex Class I Expression in *Chlamydia*-Infected Cells" *J. Exp. Med.* 191(9):1525-1534 (2000).

Zhong et al. "Identification of a Chlamydial Protease-Like Activity Factor Responsible for the Degradation of Host Transcription Factors" *J. Exp. Med.* 193(8):935-942 (2001).

Zhong et al. "Immunogenicity Evaluation of a Lipidic Amino Acid-Based Synthetic Peptide Vaccine for *Chlamydia trachomatis*" *The Journal of Immunology* 151:3728-3736 (1993).

Zhong et al. "Inhibition of Staurosporine-Induced Activation of the Proapoptotic Multidomain Bcl-2 Proteins Bax and Bak by Three Invasive Chlamydial Species" *Journal of Infection* 53(6):408-414 (2006).

Zhong et al. "Mapping Antigenic Sites on the Major Outer Membrane Protein of *Chlamydia trachomatis* with Synthetic Peptides" *Infection and Immunity* 58(5):1450-1455 (1990).

Zhong et al. "Mapping Epitopes of Neutralizing Monoclonal Antibodies Using Phage Random Peptide Libraries" *Journal of Industrial Microbiology & Biotechnology* 19:71-76 (1997).

Zhong et al. "Role of Endogenous Gamma Interferon in Host Defense Against *Chlamydia trachomatis* Infection" *Infection and Immunity* 57(1):152-157 (1989).

PCT International Preliminary Report on Patentability, mailed Apr. 21, 2011, for International Application No. PCT/US2009/005541, filed Oct. 9, 2009.

Li et al. "Characterization of Fifty Putative Inclusion Membrane Proteins Encoded in the *Chlamydia trachomatis* Genome" *Infection and Immunity* 76(6):2746-2757 (2008).

Sanchez-Campillo et al. "Identification of Immunoreactive Proteins of *Chlamydia trachomatis* by Western Blot Analysis of a Two-Dimensional Electrophoresis Map with Patient Sera" *Electrophoresis* 20:2269-2279 (1998).

Stephens et al. "Genome Sequence of an Obligate Intracellular Pathogen of Humans: *Chlamydia trachomatis*" *Science* 282:754-759 (1998).

Stephens et al. "50S Ribosomal Protein L31 Type B—*Chlamydia trachomatis*" XP002675744, Accession No. O84025 (Nov. 1, 1998) (4 pages).

Extended Search Report dated May 24, 2012 for corresponding European Application No. 09819571.2 (12 pages).

Wang et al. "A Genome-Wide Profiling of the Humoral Immune Response to *Chlamydia trachomatis* Infection Reveals Vaccine Candidate Antigens Expressed in Humans" *The Journal of Immunology*, 185:1670-1680 (2010).

Amino Acid Sequence of *Chlamydia trachomatis* CT813 protein from stdgen.northwestern.edu website, 2001 (3 pages).

Bas et al. "*Chlamydia trachomatis* Serology: Diagnostic Value of Outerf Membrane Protein 2 Compared with that of Other Antigens" *Journal of Clinical Microbiology* 39(11):4082-4085 (2001).

Bas et al. "Chlamydial Serology: Comparative Diagnostic Value of Immunoblotting, Microimmnofluorence Test, and Immunoassays Using Different Recombinant Proteins as Antigens" *Journal of Clinical Microbiology* 39(4):1368-1377 (2001).

Brunham et al. "*Chlamydia trachomatis* antigens: role in immunity and pathogenesis" *Infectious Agents and Disease* 3(5):218-233 (1994) (Abstract Only).

Caldwell et al. "Antigenic Analysis of Chlamydiae by Two-Dimensional Immunoelectrophoresis: II. A Trachoma-LGV-Specific Antigen" *Journal of Immunology* 115:969-975 (1975).

*Chlamydia trachomatis* Search Results for Gene ID: pCT03, Los Alamos National Laboratory Bioscience Division (Jan. 1, 2001) (2 pages).

Cheng et al. "Intracellular Interleukin-1α Mediates Interleukin-8 Production Induced by *Chlamydia trachomatis* Infection via a

(56) References Cited

OTHER PUBLICATIONS

Mechanism Independent of Type I Interleukin-1 Receptor" *Infection and Immunity* 76(3):942-951 (2008).
Chothia et al. "The relationship between the divergence of sequence and structure in proteins" *The EMBO Journal* 5(4):823-826 (1986).
Clifton et al. "A chlamydial type III translocated protein is tyrosine-phosphorylated at the site of entry and associated with recruitment of actin" *PNAS* 101(27):10166-10171 (2004).
Comanducci et al. "Humoral Immune Response to Plasmid Protein pgp3 in Patients with *Chlamydia trachomatis* Infection" *Infection and Immunity* 62(12):5491-5497 (1994).
Comanducci et al. "Expression of a plasmid gene of *Chlamydia trachomatis* encoding a novel 28 kDa antigen" *Journal of General Microbiology* 139:1083-1092 (1993).
Donati et al. "DNA Immunization with *pgp3* Gene of *Chlamydia trachomatis* Inhibits the Spread of Chlamydial Infection from the Lower to the Upper Genital Tract in C3H/HeN Mice" *Vaccine* 21:1089-1093 (2003).
Donati et al. "Serological Response to pgp3 Protein in Animal and Human Chlamydial Infections" *Veterinary Microbiology* 135:181-185 (2009).
Ellis, R.W. Chapter 29, pp. 568-575, of "Vaccines" [Plotkin, S.A. et al. (eds) published by W.B. Saunders company (1988).
European Search Report for to European Application No. 12161888; Sep. 14, 2012 (6 Pages).
Extended European Search Report for European Application No. 08743427; dated Sep. 1, 2011 (15 pages).
GenBank® Database Accession No. NP_220333, Hypothetical protein [*Chlamydia trachomatis*] 264 aa, Sep. 10, 2001 (1 page).
Ghaem-Maghami et al. "Mucosal and Systemic Immune Responses to Plasmid Protein pgp3 in Patients with Genital and Ocular *Chlamydia trachomatis* Infection" *Clin Exp Immunol* 132:436-442 (2003).
Grayston et al. "Trachoma Vaccine Studies on Taiwan" *Ann NY Acad Sci* 98:353-367 (1962).
Hackstadt, et al., "Origins and functions of the chlamydial inclusion" *Trends in Microbiology*, 5(7):288-293, Jul. 1997.
Hackstadt "The diverse habitats of obligate intracellular parasites" *Current Opinion in Microbiology* 1(1):82-87 (1998).
Hackstadt et al. "The *Chlamydia trachomatis* IncA protein is required for homotypic vesicle fusion" *Cellular Microbiology* 1(2):119-130 (1999).
Jensen et al. "Novel overlapping coding sequences in *Chlamydia trachomatis*" *FEMS Microbiology Letter* 265:106-117 (2006).
Jorgensen et al. "Pmp-Like Proteins Pls1 and Pls2 Are Secreted into the Lumen of the *Chlamydia trachomatis* Inclusion" *Infection and Immunity* 76(9):3940-3950 (2008).
Kinnunen et al. "HLA DQ alleles and interleukin-10 polymorphism associated with *Chlamydia trachomatis*-related tubal factor infertility: a case-control study" *Human Reproduction* 17(8):2073-2078 (2002).
Laverda et al. "Seroreactivity to *Chlamydia trachomatis* Hsp10 Correlates with Severity of Human Genital Tract Disease" *Infection and Immunity* 68(1):303-309 (2000).
Li et al. "Antibodies from Women Urogenitally Infected *C. trachomatis* Predominantly Recognized the Plasmid Protein pgp3 in a Conformation-Dependent Manner" *BMC Microbiology* 8(90):1-13 (2008).
Li et al. "Immunization with Chlamydial Plasmid Protein pORF5 DNA Vaccine Induces Protective Immunity Against Genital Chlamydial Infection in Mice" *Sci China Ser C-Life Sci* 51(11:973-980 (2008).

Molina et al. "Identification of Immunodominant Antigens of *Chlamydia trachomatis* Using Proteome Microarrays" *Vaccine* 28:3014-3024 (2010).
Peeling et al. "Antibody to Chlamydial hsp60 Predicts an Increased Risk for Chlamydial Pelvic Inflammatory Disease" *The Journal of Infectious Diseases* 175:1153-1158 (1997).
PCT International Search Report mailed Jan. 4, 2012 for PCT International Application No. PCT/US2011/027678 (9 pages).
PCT Written Opinion of the International Searching Authority mailed Jan. 4, 2012 for PCT International Application No. PCT/US2011/027678 (13 pages).
PCT International Preliminary Report on Patentability mailed Sep. 20, 2012 for PCT International Application No. PCT/US2011/027678 (14 pages).
International Search Report and Written Opinion of International Application No. PCT/US2009/05541, mailed Feb. 3, 2010 (13 pages).
Rasmussen et al. "Secretion of Proinflammatory Cytokines by Epithelial Cells in Response to *Chlamydia* Infection Suggests a Central Role for Epithelial Cells in Chlamydial Pathogenesis" *J. Clin Invest* 99:77-87 (1997).
Rockey et al. "*Chlamydia psittaci* IncA is phosphorylated by the host cell and is exposed on the cytoplasmic face of the developing inclusion" *Molecular Microbiology* 24(1):217-228.
Rockey et al, "*Chlamydia* Vaccine Candidates and Tools for Chlamydial Antigen Discovery" *Expert Rev. Vaccines* 8(10):1365-1377 (2009).
Scidmore et al. "Mammalian 14-3-3β associates with the *Chlamydia trachomatis* inclusion membrane via its interaction with IncG" *Molecular Microbiology* 39(6):1638-1650 (2001).
Shaw et al. "Characterization of a secreted *Chlamydia* protease" *Cellular Microbiology* 4(7):411-424 (2002).
Sharma et al. "Heat-Inactivated *C. pneumoniae* Organisms are not Atherogenic" *Molecular and Cellular Biochemistry* 260:147-152 (2004).
Sherman et al. "Sexually Transmitted Diseases and Tubal Pregnancy" *Sexually Transmitted Diseases* 17(3):115-121 (1990).
Stephens "The cellular paradigm of chlamydial pathogenesis" *Trends in Microbiology* 11(1):44-51 (2003).
UniProt Database Accession No. O84812, Nov. 1, 1998, 4 Pages.
Wang et al. "A chlamydial type III-secreted effector protein (Tarp) is predominantly recognized by antibodies from humans infected with *Chlamydia trachomatis* and induces protective immunity against upper genital tract pathologies in mice" *Vaccine* 27(22):2967-2980 (2009).
Yi et al. "Autoimmunity to Heat Shock Protein 60 and Antigen-Specific Production of Interleukin-10" *Infection and Immunity* 65(5):1669-1674 (1997).
Zhong et al. "Evidence That Binding Site Occupancy Is Necessary and Sufficient for Effective Major Histocompatibility Complex (MHC) Class II Transport through the Secretory Pathway Redefines the primary Function of Class II-associated Invariant Chain Peptides (CLIP)" *The Journal of Experimental Medicine* 184:2061-2066 (1996).
Zhong et al. "Production, specificity, and functionality of monoclonal antibodies to specific peptide-major histocompatibility complex class II complexes formed by processing of exogenous protein" *Proc. Natl. Acad. Sci. USA* 94:13856-13861 (1997).
Zhong "Killing me softly: chlamydial use of proteolysis for evading host defenses" *Trends in Microbiology* 17(10):467-474 (2009).

\* cited by examiner

METHODS AND COMPOSITIONS FOR CHLAMYDIAL ANTIGENS FOR DIAGNOSIS AND TREATMENT OF CHLAMYDIAL INFECTION AND DISEASE

STATEMENT OF PRIORITY

This application is a 35 U.S.C. §371 national phase application of International Application Serial No. PCT/US2009/005541, filed Oct. 9, 2009, which claims the benefit, under 35 U.S.C. §119(e), of U.S. Provisional Application No. 61/104,017, filed Oct. 9, 2008, the entire contents of each of which are incorporated by reference herein in their entireties.

STATEMENT OF GOVERNMENT SUPPORT

The present invention was funded in part by government support under grant number RO1 A164537 from the National Institutes of Health. The United States Government has certain rights in this invention.

BACKGROUND OF THE INVENTION

1. Field of the Invention

The present invention relates to the field of diagnosis of chlamydial infection and disease as well as treatment/prevention of chlamydial infection and disease.

2. Background Art

Chlamydia trachomatis infection is a leading cause of sexually transmitted bacterial diseases. Although antibiotics can be used effectively to treat chlamydial infection, it is hard to determine when and whom to treat due to the asymptomatic nature of the infection. Once persistent infection occurs and pathologies develop, it can be too late to treat. Thus, there exists a need in the art for more rapid and accurate diagnostics and more effective and available therapeutics for treatment and/or prevention of Chlamydia infection and disease.

The present invention overcomes previous shortcomings in the art by providing chlamydial antigens that can be used to develop rapid and convenient means for diagnosing chlamydial invention and to design effective treatment protocols and vaccines for treating and preventing chlamydial infection and diseases.

The antigens of the present invention have been identified by an approach employing fusion proteins covering the entire genome as antigens to screen human antibody responses, thereby allowing for a more accurate determination of the relative immunodominance of chlamydial antigens. Prior studies have used either predefined antigens or denatured antigens derived from whole organisms for similar analyses. For example, antibody responses to CT681 (MOMP) have been linked to protective immunity, while antibody responses to CT110 (HSP60) have been linked to chlamydial pathogenicity. The more comprehensive approach employed in the present invention allows for the identification of more relevant and important chlamydial antigens.

By co-relating the antibody response profiles with patient clinical symptomology, antigens can be identified that are involved in pathogenesis and can thus be developed as diagnostic markers. Furthermore, antigens can be identified that are involved in protective immunity for use as vaccine candidates.

SUMMARY OF THE INVENTION

The present invention provides a composition comprising one or more than one (e.g., 2, 3, 4, 5, 6, 7, 8, 9, 10, etc.) isolated Chlamydia trachomatis protein selected from the group consisting of (1) CT005, (2) CT019, (3) CT022, (4) CT046, (5) CT067, (6) CT099, (7) CT111, (8) CT116, (9) CT118, (10) CT149, (11) CT153, (12) CT208, (13) CT225, (14) CT228, (15) CT236, (16) CT237, (17) CT242, (18) CT260, (19) CT278, (20) CT322, (21) CT328, (22) CT376, (23) CT396, (24) CT414, (25) CT431, (26) CT450, (27) CT457, (28) CT494, (29) CT507, (30) CT532, (31) CT542, (32) CT556, (33) CT578, (34) CT673, (35) CT733, (36) CT743, (37) CT759, (38) CT791, (39) CT798, (40) CT828, and (41) CT868, an immunogenic fragment of any of (1)-(41), a homologue of any of (1)-(41) from a different Chlamydia species and any combination thereof.

In additional embodiments, the compositions of this invention can further comprise an isolated Chlamydia trachomatis protein selected from the group consisting of (42) CT110 (HSP60), (43) CT119 (IncA), (44) CT858 (CPAF) CT681 (MOMP), an immunogenic fragment of any of (42)-(44), a homologue of (42)-(44) from a different Chlamydia species and any combination.

In yet further embodiments, any of the compositions of this invention can comprise one or more than one (e.g., 2, 3, 4, 5, 6, 7, 8, 9, 10, etc.) isolated Chlamydia trachomatis protein selected from the group of any of proteins 1-78 of Table 1, any of proteins 1-19 of Table 2, an immunogenic fragment thereof, a homologue thereof from a different Chlamydia species and any combination thereof.

The compositions of this invention can be in a pharmaceutically acceptable carrier and in some embodiments can further comprise an adjuvant and/or an immunostimulant, which can be, but is not limited to, CpG, IL-12 and any combination thereof.

The present invention further provides embodiments wherein the compositions of this invention can also comprise a protein or immunogenic fragment thereof of a pathogenic organism other than Chlamydia trachomatis. Such pathogenic organism can be, but is not limited to Chlamydia muridarium, Chlamydia pneumoniae, Chlamydia caviae. Trichomonas vaginalis, Candida albicans, Neisseria gonorrheae, Treponema pallidum, Herpes simplex virus, human papilloma virus and human immunodeficiency virus and any combination thereof.

The present invention additionally provides a method of detecting an antibody to Chlamydia in a sample, comprising: a) contacting the sample with the composition of this invention under conditions whereby an antigen/antibody complex can form; and b) detecting antigen/antibody complex formation, thereby detecting an antibody to Chlamydia in the sample.

Also provided herein is a: method of diagnosing a Chlamydia infection in a subject, comprising: a) contacting a sample from the subject with the composition of this invention under conditions whereby an antigen/antibody complex can form; and b) detecting antigen/antibody complex formation, thereby diagnosing a Chlamydia infection in the subject.

The present invention further provides a method of detecting a Chlamydia protein in a sample, comprising: a) contacting the sample with an antibody that specifically binds a protein or immunogenic fragment thereof of this invention under conditions whereby an antigen/antibody complex can form; and b) detecting antigen/antibody complex formation, thereby detecting a Chlamydia protein in the sample.

In addition, a method is provided of diagnosing a Chlamydia infection in a subject, comprising: a) contacting a sample from the subject with an antibody that specifically binds a protein or immunogenic fragment thereof of this invention under conditions whereby an antigen/antibody complex can form; and b) detecting antigen/antibody complex formation, thereby diagnosing a *Chlamydia* infection in the subject.

In yet further embodiments, the present invention provides a method of eliciting an immune response in a subject, comprising administering to the subject an effective amount of the composition of this invention, thereby eliciting an immune response in the subject.

Also provided herein is a method of treating or preventing an infection by *Chlamydia* in a subject, comprising administering to the subject an effective amount of the composition of this invention, thereby treating or preventing an infection by *Chlamydia* in the subject.

Further aspects of the present invention include a method of reducing the likelihood of infertility due to *Chlamydia* infection in a subject, comprising administering to the subject an effective amount of a protein or immunogenic fragment thereof of this invention. In some embodiments, the method can further comprise administering an adjuvant to the subject.

In additional embodiments, the present invention provides a method of reducing the incidence of hydrosalpinx due to *Chlamydia* infection in a subject, comprising administering to the subject a composition comprising an effective amount of a protein or an immunogenic fragment thereof of this invention. In some embodiments, the method can further comprise administering an adjuvant to the subject.

DETAILED DESCRIPTION OF THE INVENTION

The present invention is based on the unexpected discovery of immunodominant proteins of *Chlamydia trachomatis*. These immunodominant proteins have been identified by the screening fusion protein arrays described herein in the EXAMPLES section. These immunodominant proteins, immunogenic fragments thereof and/or homologues of these proteins or immunogenic fragments from other chlamydial species can be employed in methods of detection and diagnosis by identifying the presence of the protein or the presence of an antibody to the protein in a sample, such as a biological sample from a subject. Furthermore, these proteins, immunogenic fragments there and/or homologues of these proteins and/or immunogenic fragments thereof from other chlamydial species can be employed in methods of treating infection and disease caused by *Chlamydia* as well as in methods of prophylaxis (e.g., as a vaccine) to prevent infection and disease caused by *Chlamydia*.

Thus, as set forth herein, the present invention provides a composition comprising one or more than one (e.g., 2, 3, 4, 5, 6, 7, 8, 9, 10, etc.) isolated *Chlamydia trachomatis* protein selected from the group consisting of (1) CT005, (2) CT019, (3) CT022, (4) CT046, (5) CT067, (6) CT099, (7) CT 111, (8) CT 116, (9) CT 118, (10) CT149, (11) CT153, (12) CT208, (13) CT225, (14) CT228, (15) CT236, (16) CT237, (17) CT242, (18) CT260, (19) CT278, (20) CT322, (21) CT328, (22) CT376, (23) CT396, (24) CT414, (25) CT431, (26) CT450, (27) CT457, (28) CT494, (29) CT507, (30) CT532, (31) CT542, (32) CT556, (33) CT578, (34) CT673, (35) CT733, (36) CT743, (37) CT759, (38) CT791, (39) CT798, (40) CT828, and (41) CT868, an immunogenic fragment of any of (1)-(41), a homologue of any of (1)-(41) from a different *Chlamydia* species and any combination thereof.

In additional embodiments, the compositions of this invention as recited above can further comprise an isolated *Chlamydia trachomatis* protein selected from the group consisting of (42) CT110 (HSP60), (43) CT119 (IncA), (44) CT858 (CPAF) CT681 (MOMP), an immunogenic fragment of any of (42)-(44), a homologue of (42)-(44) from a different *Chlamydia* species and any combination.

In yet further embodiments, any of the compositions of this invention can comprise one or more than one (e.g., 2, 3, 4, 5, 6, 7, 8, 9, 10, etc.) isolated *Chlamydia trachomatis* protein selected from the group of any of proteins 1-78 of Table 1, any of proteins 1-19 of Table 2, an immunogenic fragment thereof, a homologue thereof from a different *Chlamydia* species and any combination thereof.

In addition, the present invention provides a composition comprising an isolated *Chlamydia trachomatis* CT806 protein, CT823 protein, CT841 protein, pCT03 protein CT813 protein, a homologue of a CT806, CT823, CT841, pCT03 or CT813 protein from a different *Chlamydia* species, and/or an immunogenic fragment thereof in a pharmaceutically acceptable carrier. These proteins, homologues and immunogenic fragments can be present in a composition of this invention in any combination and in any ratio relative to one another.

The present invention further provides a composition comprising two or more isolated *Chlamydia trachomatis* proteins which can be: (a) CH089 (CopN), (b) CT147 (EEA homology), (c) CT226 (Inc), (d) CT442 (15 kDa Crp), (e) CT443 (60 kDa CRP, OmcB), (f) CT529 (Inc, CapA), (g) CT694 (HP, IB), (h) CT795 (HP, IB), (i) CT806, (j) CT812 (pmpD), (k) CT813 (Inc), (1) CT823, (m) CT841, (n) pCT03, an immunogenic fragment of any of (o)-(n), a homologue of any of (a)-(n) from a different *Chlamydia* species and any combination thereof.

In additional embodiments, the compositions of this invention can further comprise an isolated *Chlamydia trachomatis* protein which can be: (o) CT110 (HSP60), (p) CT119 (IncA), (q) CT858 (CPAF), an immunogenic fragment of any of (o)-(q), a homologue of (o)-(q) from a different *Chlamydia* species and any combination thereof. As noted herein, the chlamydial proteins, immunogenic fragments and homologues of this invention can be present in any combination and in any ratio relative to one another.

The present invention further provides an isolated nucleic acid encoding a *Chlamydia* protein or immunogenic fragment thereof of this invention, the nucleotide sequences of which are well known in the art. Such nucleic acids can be present in a vector (e.g., a viral vector such as vaccinia virus, adenovirus, adeno-associated virus, lentivirus, herpes virus, alphavirus vectors, etc., as are well known in the art), which can be present in a cell (e.g., a cell transformed by the introduction of heterologous nucleic acid). The nucleic acids, vectors and/or cells of this invention can be used in the methods of this invention. For example, nucleic acid encoding a protein of this invention can be detected by contacting a sample suspected of containing a nucleic acid of this invention with a nucleotide sequence that is complementary to the nucleic acid (e.g., as a probe or primer) under conditions whereby a hybridization complex can form and detecting the formation of the hybridization complex, thereby detecting the nucleic acid of this invention in the sample. Nucleic acid hybridization protocols for detection of nucleic acids as well as diagnosis of infection and disease are well known in the art.

The detection of a nucleic acid or nucleotide sequence of this invention can be carried out according to various protocols standard in the art and as described herein for analyzing nucleic acid samples and nucleotide sequences, as well as identifying specific nucleotides in a nucleotide sequence.

For example, nucleic acid can be obtained from any suitable sample from the subject that will contain nucleic acid and the nucleic acid can then be prepared and analyzed according to well-established protocols. In some embodiments, analysis of the nucleic acid can be carried by sequencing the nucleic acid strand and/or its complement, by hybridization reactions and/or by amplification of the region of interest according to amplification protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA), etc.). In some embodiments, the amplification product can be visualized directly in a gel by staining or the product can be detected by hybridization with a detectable probe or by translation into a gene product. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

In additional embodiments of this invention, the chlamydial proteins listed in Table II can also be employed in the methods and compositions of this invention, either singly or in any combination (e.g., 2, 3, 4, 5, 6, 7, 8, 9, 10 or more) with one another and/or in combination with any other chlamydial protein and/or reagent of this invention.

The present invention further provides isolated nucleic acids, vectors and cells of this invention for use in the treatment and prevention methods described herein. Thus, in particular embodiments, a nucleic acid of this invention encoding a *Chlamydia* protein or immunogenic fragment thereof of this invention can be introduced into a subject, wherein the nucleic acid is expressed and the encoded product is produced to elicit an immune response in the subject, thereby treating or preventing a *Chlamydia* infection and/or disease. Thus, the nucleic acids, vectors and/or cells of this invention can be present in a composition comprising a pharmaceutically acceptable carrier.

As used herein, "a," "an" or "the" can mean one or more than one (e.g., 2, 3, 4, 5, 6, 7, 8, 9, 10, etc.). For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, by "pharmaceutically acceptable" is meant a material that is not biologically or otherwise undesirable, i.e., the material may be administered to a subject without causing appreciable undesirable biological effects. Thus, such a pharmaceutical composition may be used, for example, to prepare compositions for immunization. Physiologically and pharmaceutically acceptable carriers may contain other compounds including but not limited to stabilizers, salts, buffers, adjuvants and/or preservatives (e.g., antibacterial, antifungal and antiviral agents) as are known in the art. The pharmaceutically acceptable carrier can be sterile in some embodiments.

The term "isolated" as used herein means the protein or polypeptide or immunogenic fragment or nucleic acid of this invention is sufficiently free of contaminants or cell components with which polypeptides and/or nucleic acids normally occur. "Isolated" does not mean that the preparation is technically pure (homogeneous), but it is sufficiently pure to provide the polypeptide or nucleic acid in a form in which it can be used therapeutically.

"Epitope" or "antigenic epitope" or "antigenic peptide" as used herein means a specific amino acid sequence of limited length (e.g., 5-12 amino acids or 3-10 amino acids or 4-8 amino acids or 6-15 amino acids) which, when present in the proper conformation, provides a reactive site for an antibody or T cell receptor. The identification of epitopes on antigens can be carried out by immunology protocols that are well known in the art. An "immunogenic fragment" of this invention can comprise one, two, three, four or more epitopes of a protein of this invention.

As used herein, the term "polypeptide" or "protein" is used to describe a chain of amino acids that correspond to those encoded by a nucleic acid. A polypeptide or protein of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences of this invention are presented in the amino to carboxy direction, from left to right. Nucleotide sequences are presented herein by single strand only, in the 5' to 3' direction, from left to right. However, it is intended that the nucleic acids of this invention can be either single or double stranded (i.e., including the complementary nucleic acid). A nucleic acid of this invention can be the complement of a nucleic acid described herein.

A "biologically active fragment" includes a polypeptide of this invention that comprises a sufficient number of amino acids to have one or more of the biological activities of the polypeptides of this invention. Such biological activities can include, but are not limited to, in any combination, binding activity and/or immunogenic activity, as well as any other activity now known or later identified for the polypeptides and/or fragments of this invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments and/or immunogenic fragments of the polypeptides described herein would be well within the scope of one of ordinary skill in the art and would be routine.

As used herein, the term "antibody" includes intact immunoglobin molecules as well as fragments thereof, such as Fab, F(ab')2, and Fc, which are capable of binding the epitopic determinant of an antigen (i.e., antigenic determinant). Antibodies that bind the polypeptides of this invention are prepared using intact polypeptides or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art.

The term "antibody" or "antibodies" as used herein refers to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980. The antibody can further be a single chain antibody or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein, (1975) *Nature* 265:495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope of interest.

The term "sample" as used herein is used in its broadest sense. A biological sample suspected of containing a polypeptide, fragment, antibody and/or nucleic acid of this invention can be any biological fluid, an extract from a cell, an extracellular matrix isolated from a cell, a cell (in solution or bound to a solid support), a tissue, a tissue print, and the like.

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

As used herein, the term "consists essentially of" (and grammatical variants) means that the immunogenic composition comprises no other material immunogenic agent other than the indicated agents. The term "consists essentially of" does not exclude the presence of other components such as adjuvants, immunomodulators, and the like.

The invention can be practiced to protect a subject against infection and/or disease caused by chlamydial species, including, for example, *Chlamydia trachomatis, Chlamydia muridarium* and *Chlamydia pneumoniae*. By "protect," "protecting," and "protection" and like terms it is meant any level of protection which is of some benefit in a population of subjects, such that there is a reduction in the incidence and/or the severity of the disease among treated subjects, regardless of whether the protection is partial or complete.

By "prime," "primed" or "priming" (and grammatical variations thereof) as used herein, it is meant to initiate an active immune response that is less than the protective until a second dose (booster) has given at a later time post hatch.

By "reduce," "reduced," "reducing," and "reduction" (and grammatical variations thereof), as used herein, it is meant a decrease in a chlamydial infection- or disease-related parameter that is of some value or benefit.

The invention can also be practiced to induce an immune response to *Chlamydia*. As used herein, the term "induce (or grammatical variations thereof) an immune response against *Chlamydia*" is intended to encompass agents that induce an immune response against the organism itself and/or, e.g., toxins or secreted proteins produced by the organism, by means of passive transfer and/or active immune response. Optionally, the immune response that is induced is a protective immune response, for example, in vaccination methods. Protection is not required if there is some other purpose for inducing the immune response, for example, for research purposes or to produce antibody for passive immunizations or as a reagent (e.g., to detect, isolate and/or identify *Chlamydia* species).

The terms "immunogenic amount" or "effective amount" or "effective immunizing dose," as used herein, unless otherwise indicated, mean a dose of a composition of this invention sufficient to induce a protective immune response in the treated subject that is greater than the inherent immunity of non-immunized subjects. An immunogenic amount or effective amount or effective immunizing dose in any particular context can be routinely determined using methods known in the art.

In some embodiments, an effective immunizing dose or immunogenic amount or effective amount can comprise one or more (e.g., two or three) doses of the immunogenic composition so as to achieve the desired level of protection.

The terms "vaccine," "vaccination" or "immunization" are well-understood in the art, and are used interchangeably herein. For example, the terms vaccine, vaccination or immunization can be understood to be a process or composition that increases a subject's immune reaction to antigen (by providing an active immune response), and therefore its ability to resist, overcome and/or recover from infection (i.e., a protective immune response).

The terms "protective immunity" or "protective immune response," as used herein, are intended to mean that the host animal mounts an active immune response to the immunogenic composition and/or that the immunogenic composition provides passive immunity, such that upon subsequent exposure or a challenge, the animal is able to resist or overcome infection and/or disease. Thus, a protective immune response will decrease the incidence of morbidity and/or mortality from subsequent exposure to the pathogen.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A subject of this invention includes any animal susceptible to infection by *Chlamydial* species. Such a subject can be a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species and in particular embodiments, is a human. A "subject in need thereof" is a subject known to be, or suspected of being, infected with *Chlamydia*. A subject of this invention can also include a subject not previously known or suspected to be infected by *Chlamydia* or in need of treatment for *Chlamydia* infection. For example, a subject of this invention can be administered the compositions of this invention even if it is not known or suspected that the subject is infected with *Chlamydia* (e.g., prophylactically). A subject of this invention is also a subject known or believed to be at risk of infection by *Chlamydia*.

In certain embodiments, the fragments and/or polypeptides of this invention can be fused with a "carrier" protein or peptide to produce a fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescent protein (GFP), β-glucoronidase, β-galactosidase, luciferase, and the like) for easy detection. As a further alternative, the fusion protein attached to the polypeptides and/or fragments and a carrier protein or peptide can be targeted to a subcellular compartment of interest, i.e., to affect the co-localization of the polypeptide and/or fragment. Any suitable carrier protein as is well known in the art can be used to produce a fusion protein of this invention.

A variety of protocols for detecting the presence of and/or measuring the amount of polypeptides, fragments and/or peptides in a sample, using either polyclonal or monoclonal antibodies specific for the polypeptide, fragment and/or peptide are known in the art. Examples of such protocols include, but are not limited to, enzyme immunoassays (EIA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS). These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

The present invention further includes isolated polypeptides, peptides, proteins and/or fragments that are substantially equivalent to those described for this invention. As used herein, "substantially equivalent" can refer both to nucleic acid and amino acid sequences, for example a mutant sequence, that varies from a reference sequence by one or more substitutions (e.g., substitution with conservative amino acids as are well known in the art), deletions and/or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologues, as well as methods of obtaining homologues, of the polypeptides and/or fragments of this invention from other strains of *Chlamydia* and/or other organisms included in this invention. As used herein, an amino acid sequence or protein is defined as a homologue of a polypeptide or fragment of the present invention if it shares significant homology or identity with one of the polypeptides and/or fragments of the present invention. Significant homology or identity means at least 50%, 55%, 60%, 65%, 70%, 75%, 80%, 85%, 90%, 95%, 98% and/or 100% homology or identity with another amino acid sequence. Such homologues can also be identified by having significant identity at the nucleotide sequence level (i.e., at least 50%, 55%, 60%, 65%, 70%, 75%, 80%, 85%, 90%, 95%, 98% and/or 100% or identity with another nucleotide sequence).

As one example, by using the nucleic acids that encode the chlamydial proteins or fragments of this invention (as are known in the art and incorporated by reference herein), as a probe or primer, and techniques such as PCR amplification and colony/plaque hybridization, one skilled in the art can identify homologues of the polypeptides and/or fragments of this invention in *Chlamydia* and/or other organisms on the basis of information available in the art.

As another example, homologues of the chlamydial proteins of this invention can be identified by having cross-reactivity when analyzed in immunoassays employing antibodies that specifically react with a chlamydial protein or immunogenic fragment of this invention.

As one non-limiting example, a listing of *Chlamydia pneumoniae* proteins and the *Chlamydia trachomatis* homologues of these proteins can be found in U.S. Pat. No. 6,822,071, the entire contents of which are incorporated by reference herein for these teachings.

The present invention also provides an antibody that specifically binds the polypeptides and/or immunogenic fragments of this invention, as well as a method of making an antibody specific for a polypeptide and/or fragment of this invention comprising: a) immunizing an animal with a polypeptide and/or fragment of this invention under conditions whereby the animal produces antibodies that specifically bind the polypeptide and/or fragment of this invention; and b) removing biological materials comprising the antibodies from the animal. Also provided herein is an antibody produced by the methods set forth herein.

Antibodies of this invention can be generated using methods that are well known in the art. Such antibodies and immunoglubin molecules of this invention can include, but are not limited to, polyclonal antibodies, monoclonal antibodies, chimeric antibodies, humanized antibodies, single chain antibodies (e.g., scFv), Fab fragments, and fragments produced by a Fab expression library.

In general, techniques for preparing polyclonal and monoclonal antibodies as well as hybridomas capable of producing a desired antibody are well known in the art. Any animal known to produce antibodies can be immunized with a polypeptide, fragment and/or antigenic epitope of this invention. Methods for immunization of animals to produce antibodies are well known in the art. For example, such methods can include subcutaneous or intraperitoneal injection of the polypeptide, fragment and/or antigenic epitope of this invention.

The polypeptide, fragment or antigenic epitope that is used as an immunogen can be modified and/or administered in an adjuvant in order to increase antigenicity. Methods of increasing the antigenicity of a protein or peptide are well known in the art and include, but are not limited to, coupling the antigen with a heterologous protein (such as globulin or β-galactosidase) and/or through the inclusion of an adjuvant during immunization.

For example, for the production of antibodies, various hosts including goats, rabbits, rats, mice, humans, and others, can be immunized by injection with the polypeptides and/or fragments of this invention, with or without a carrier protein. Additionally, various adjuvants may be used to increase the immunological response. Such adjuvants include, but are not limited to, Freund's complete and incomplete adjuvants, mineral gels such as aluminum hydroxide, and surface-active substances such as lysolecithin, pluronic polyols, polyanions, peptides, oil emulsions, keyhole limpet hemocyanin, and dinitrophenol. Nonlimiting examples of adjuvants used in humans include BCG (bacilli Calmette-Guerin) and *Corynebacterium parvum*.

Polypeptides, peptides and/or fragments of this invention used as antigens to produce the antibodies of this invention can have an amino acid sequence consisting of at least about five amino acids and in certain embodiments, at least about ten amino acids. In one embodiment, the antigen is identical to a portion of the amino acid sequence of the natural protein, and it can contain the entire amino acid sequence of a small, naturally-occurring molecule. Short stretches of the polypeptides and/or fragments of this invention can be fused with all or a fragment of another protein that acts as a carrier protein (e.g., keyhole limpet hemocyanin) and antibodies can be produced against the chimeric polypeptide or peptide.

Monoclonal antibodies to the polypeptides and/or fragments of this invention are prepared using any technique, which provides for the production of antibody molecules by continuous cell lines in culture. These include, but are not limited to, the hybridoma technique, the human B-cell hybridoma technique, and the EBV-hybridoma technique (Kohler et al. 1975. *Nature* 256:495-497; Kozbor et al. 1985.1 *J.* *Immunol. Methods* 81:31-42; Cote et al. 1983. *Proc. Natl. Acad. Sci.* 80:2026-2030; Cole et al. 1984. *Mol. Cell Biol.* 62:109-120).

For example, to produce monoclonal antibodies, spleen cells from the immunized animal are removed, fused with myeloma cells, and cultured in selective medium to become monoclonal antibody-producing hybridoma cells, according to techniques routine in the art. Any one of a number of methods well known in the art can be used to identify the hybridoma cell, which produces an antibody with the desired characteristics. These include screening the hybridomas by ELISA assay, Western blot analysis, or radioimmunoassay. Hybridomas secreting the desired antibodies are cloned and the class and subclass are identified using standard procedures known in the art.

For polyclonal antibodies, antibody-containing serum is isolated from the immunized animal and is screened for the presence of antibodies with the desired specificity using any of the well known procedures as described herein.

The present invention further provides antibodies of this invention in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescence labels (such as FITC or rhodamine, etc.), paramagnetic atoms, gold beads, etc. Such labeling procedures are well-known in the art. The labeled antibodies of the present invention can be used for in vitro, in vivo, and in situ assays to identify a polypeptide and/or fragment of this invention in a sample.

In some embodiments, the present invention further provides the antibodies and/or antigens of this invention immobilized on a solid support (e.g., beads, plates, slides or wells formed from materials such as, e.g., latex or polystyrene). Nonlimiting examples of such solid supports include polycarbonate, agarose, nitrocellulose, sepharose, acrylic resins, polyacrylamide and latex beads, as well as any other solid support known in the art. Techniques for coupling antibodies and antigens to such solid supports are well known in the art (Weir et al., *Handbook of Experimental Immunology* 4th Ed., Blackwell Scientific Publications, Oxford, England, Chapter 10 (1986)). Antibodies and/or antigens of this invention can likewise be conjugated to detectable groups such as radiolabels (e.g., $^{35}$S, $^{125}$I, $^{131}$I), enzyme labels (e.g., horseradish peroxidase, alkaline phosphatase), and fluorescence labels (e.g., fluorescein) in accordance with known techniques. Conditions suitable for the formation of an antigen/antibody complex are routine in the art and form the basis for all immunoassays. Such conditions may vary depending on the particular reagents, samples and/or steps employed in a given immunoassay, as would be readily determined by one of ordinary skill in the art. Determination of the formation of an antibody/antigen complex in the methods of this invention can be by detection of, for example, precipitation, agglutination, flocculation, radioactivity, color development or change, fluorescence, luminescence, etc., as is well know in the art.

In addition, techniques developed for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and fragments of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

Antibody fragments that specifically bind the polypeptides and/or fragments of this invention can also be generated. For example, such fragments include, but are not limited to, the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed to allow rapid and easy identification of monoclonal Fab fragments with the desired specificity (Huse et al. 1989. *Science* 254:1275-1281).

Various immunoassays can be used for screening to identify antibodies having the desired specificity for the proteins and peptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). For example, a two-site, monoclonal-based immunoassay utilizing monoclonal antibodies reactive to two non-interfering epitopes on the proteins or peptides of this invention can be used, as well as a competitive binding assay.

It is further contemplated that the present invention provides kits for detection of the polypeptides and/or fragments and/or antibodies of this invention in a sample. In one embodiment, the kit can comprise one or more antibodies of this invention, along with suitable buffers, wash solutions and/or other reagents for the detection of antibody/antigen complex formation. In an alternative embodiment, a kit of this invention can comprise a polypeptide, an antigenic peptide of the polypeptide of this invention, a fragment of this invention and/or an antigenic peptide of a fragment of this invention, along with suitable buffers, wash solutions and/or other reagents for the detection of antibody/antigen complex formation.

The present invention further provides a kit for the detection of nucleic acid encoding the polypeptides and/or fragments of this invention. For example, in one embodiment, the kit can comprise one or more nucleic acids of this invention, along with suitable buffers, wash solutions and/or other reagents for the detection of hybridization complex formation.

It would be well understood by one of ordinary skill in the art that the kits of this invention can comprise one or more containers and/or receptacles to hold the reagents (e.g., antibodies, antigens, nucleic acids) of the kit, along with appropriate buffers and/or wash solutions and directions for using the kit, as would be well known in the art. Such kits can further comprise adjuvants and/or other immunostimulatory or immunomodulating agents, as are well known in the art.

Furthermore, any of the compositions of this invention can comprise a suitable adjuvant. As used herein, "suitable adjuvant" describes an adjuvant capable of being combined with the polypeptide and/or fragment of this invention to further enhance an immune response without deleterious effect on the subject or the cell of the subject. A suitable adjuvant can be, but is not limited to, CpG, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

The compositions of the present invention can also include other medicinal agents, pharmaceutical agents, carriers, diluents, immunostimulatory cytokines, etc. Actual methods of preparing such dosage forms are known, or will be apparent, to those skilled in this art.

It is contemplated that the above-described compositions of this invention can be administered to a subject or to a cell of a subject to impart a therapeutic benefit. Thus, the present invention further provides a method of producing an immune response in a subject, comprising administering to the subject or to a cell of the subject an effective amount of a polypeptide and/or immunogenic fragment of this invention and/or a nucleic acid comprising a nucleotide sequence encoding a polypeptide and/or immunogenic fragment of this invention. The cell of the subject can be in vivo or ex vivo and can be, but is not limited to a CD8+ T lymphocyte (e.g., a cytotoxic T lymphocyte) or an MHC I-expressing antigen presenting cell, such as a dendritic cell, a macrophage and/or a monocyte. Detection of an immune response in the subject or in the cells of the subject can be carried out according to methods standard in the art for detecting a humoral and/or cellular immune response.

Furthermore, the present invention provides a method of eliciting an immune response in a subject, comprising administering to the subject an effective amount of a polypeptide and/of fragment of this invention.

In additional embodiments, the present invention provides a method of providing passive immunity to a subject, comprising administering to the subject an effective amount of an antibody of this invention to the subject.

The compositions of this invention can also be employed as a therapeutic and/or prophylactic formulation and administered to a subject in need thereof. Thus, the present invention provides a method of treating or preventing infection by *Chlamydia* in a subject, comprising administering to the subject an effective amount of a polypeptide and/or fragment of this invention, a nucleic acid and/or vector of this invention, and/or an antibody of this invention.

In addition, the present invention provides a method of treating or preventing infection or intoxication caused by *Chlamydia* in a subject comprising contacting an immune cell of the subject with any of the polypeptides, fragments, nucleic acids, vectors and/or antibodies of this invention. The cell can be in vivo or ex vivo and can be, for example, a CD8+ T cell which is contacted with the polypeptide and/or fragment of this invention in the presence of a class I MHC molecule, which can be a soluble molecule or it can be present on the surface of a cell which expresses class I MHC molecules. The cell can also be an antigen presenting cell or other class I MHC-expressing cell which can be contacted with the nucleic acids and/or vectors of this invention under conditions whereby the nucleic acid or vector is introduced into the cell (e.g., to produce a transformed cell) by standard methods for uptake of nucleic acid and vectors. The nucleic acid encoding the polypeptide and/or fragment of this invention is then expressed and the polypeptide and/or fragment product is processed within the antigen presenting cell or other MHC I-expressing cell and presented on the cell surface as an MHC I/antigen complex. The antigen presenting cell or other class I MHC-expressing cell is then contacted with an immune cell of the subject which binds the class I MHC/antigen complex and elicits an immune response which treats or prevents *Chlamydia* infection in the subject.

Further embodiments of the present invention include a method of reducing the likelihood of infertility due to *Chlamydia* infection in a subject, comprising administering to the subject a composition comprising an effective amount of one or more than one (e.g., 2, 3, 4, 5, 6, 7, 8, 9, 10, etc.) protein or an immunogenic fragment thereof of this invention. The method can further comprise administering an adjuvant to the subject.

By "reducing the likelihood of infertility due to *Chlamydia* infection" is meant that a subject of this invention to whom the immunogenic compositions of this invention are administered is prevented from becoming infertile as a result of *Chlamydia* infection or that the likelihood that the subject will become infertile as a result of being infected by *Chlamydia* is reduced as compared to the likelihood that an untreated subject will become infertile as a result of being infected by *Chlamydia*. The prevention or reduced likelihood or incidence of infertility results from preventing or treating *Chlamydia* infection in the subject according to the methods of this invention. That infertility is prevented or its likelihood as a result of *Chlamydia* infection is reduced in a subject can be determined according to protocols described herein and as would be well known in the art.

Hydrosalpinx is a result of tubal blockade and subsequent retention of fluid exudate within the tubal lumen. Given that the patency of oviducts is important to allow fertilization of the ovum and sperm, and that the hydrosalpinx fluid is toxic to the ovum, the presence of hydrosalpinx serves as an indirect marker of infertility.

Thus, the present invention further provides a method of reducing the incidence of hydrosalpinx due to *Chlamydia* infection in a subject, comprising administering to the subject a composition comprising an effective amount of one or more than one (e.g., 2, 3, 4, 5, 6, 7, 8, 9, 10, etc.) protein or an immunogenic fragment thereof of this invention. The method can further comprise administering an adjuvant to the subject.

By "reducing the incidence of hydrosalpinx due to *Chlamydia* infection" is meant that a subject of this invention to whom the immunogenic compositions of this invention are administered will be prevented from or protected against developing hydrosalpinx due to *Chlamydia* infection or has a reduced likelihood of developing hydrosalpinx due to *Chlamydia* infection or has a lesser degree of hydrosalpinx due to *Chlamydia* infection as compared to an untreated subject infected by *Chlamydia*. The prevention or reduced incidence of hydrosalpinx results from preventing or treating (e.g., reducing oviduct pathology) *Chlamydia* infection in the subject according to the methods of this invention. That hydrosalpinx due to *Chlamydia* infection is prevented or its incidence and/or degree are reduced in a subject can be determined according to protocols described herein and as would be well known in the art.

In some embodiments, the protein or immunogenic fragment thereof of this invention can be administered to a subject of this invention as a protein or peptide to elicit an immune response to treat and/or prevent chlamydial infections and/or to reduce the likelihood of infertility due to *Chlamydia* infection and/or to reduce the incidence of hydrosalpinx. In other embodiments, a nucleic acid or multiple nucleic acids encoding a protein or immunogenic fragment thereof of this invention in any combination can be administered to a subject of this invention to elicit an immune response to treat and/or prevent chlamydial infection and/or reduce the likelihood of infertility due to *Chlamydia* infection and/or to reduce the incidence of hydrosalpinx.

As set forth above, it is contemplated that in the methods wherein the compositions of this invention are administered to a subject or to a cell of a subject, such methods can further comprise the step of administering a suitable adjuvant to the subject or to a cell of the subject. The adjuvant can be in the composition of this invention or the adjuvant can be in a separate composition comprising the suitable adjuvant and a pharmaceutically acceptable carrier. The adjuvant can be administered prior to, simultaneous with, or after administration of the composition containing any of the polypeptides, fragments, nucleic acids and/or vectors of this invention. For example, QS-21, similar to alum, complete Freund's adjuvant, SAF, etc., can be administered within days/weeks/hours (before or after) of administration of the composition of this invention. The effectiveness of an adjuvant can be determined by measuring the immune response directed against the polypeptide and/or fragment of this invention with and without the adjuvant, using standard procedures, as described herein and as are well known in the art.

The compositions of this invention can be administered to a cell of a subject or to a subject either in vivo or ex vivo. For administration to a cell of the subject in vivo, as well as for administration to the subject, the compositions of this invention can be administered orally, parenterally (e.g., intravenously), by intramuscular injection, by intraperitoneal injection, subcutaneous injection, transdermally, extracorporeally, topically or the like. Also, the compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount of the composition required will vary from subject to subject, depending on the species, age, weight and general condition of the subject, the particular composition used, its mode of administration and the like. Thus, it is not possible to specify an exact amount for every composition of this invention. However, effective amount can be determined by one of ordinary skill in the art using only routine experimentation given the teachings herein.

The composition of this invention can be administered to a subject prior to, during and/or after *Chlamydia* infection. As an example, to a subject diagnosed with *Chlamydia* infection or known to be at risk of being infected with *Chlamydia* or in whom it is desirable to induce an immune response to *Chlamydia*, between about 50-1000 nM, or between about 100-500 nM of a polypeptide and/or immunogenic fragment of this invention can be administered, e.g., subcutaneously, and can be in an adjuvant, at one to three hour/day/week intervals until an evaluation of the subject's clinical parameters indicate that the subject is not infected by *Chlamydia* and/or the subject demonstrates the desired immunological response. Alternatively, a polypeptide and/or fragment of this invention can be pulsed onto dendritic cells at a concentration of between about 10-100 µM and the dendritic cells can be administered to the subject intravenously at the same time intervals. The treatment can be continued or resumed if the subject's clinical parameters indicate that *Chlamydia* infection is present and can be maintained until the infection is no longer detected by these parameters and/or until the desired immunological response is achieved.

Parenteral administration of the peptides, polypeptides, nucleic acids and/or vectors of the present invention, if used, is generally characterized by injection. Injectables can be prepared in conventional forms, either as liquid solutions or suspensions, solid forms suitable for solution of suspension in liquid prior to injection, or as emulsions. As used herein, "parenteral administration" includes intradermal, intranasal, subcutaneous, intramuscular, intraperitoneal, intravenous and intratracheal routes, as well as a slow release or sustained release system such that a constant dosage is maintained. See, e.g., U.S. Pat. No. 3,610,795, which is incorporated by reference herein in its entirety.

The efficacy of treating or preventing *Chlamydia* infection by the methods of the present invention can be determined by detecting a clinical improvement as indicated by a change in the subject's symptoms and/or clinical parameters, as would be well known to one of skill in the art.

It is further contemplated that the compositions of the present invention can be used in diagnostic and therapeutic applications. Thus, the present invention provides a method of detecting the presence of a polypeptide and/or fragment of this invention in a sample, comprising contacting the sample with an antibody of this invention under conditions whereby an antigen/antibody complex can form and detecting formation of an antigen/antibody complex, thereby detecting the presence of a *Chlamydia* polypeptide and/or fragment of this invention in the sample.

Additionally, the present invention provides a method of detecting the presence of an antibody of this invention in a sample, comprising contacting the sample with a polypeptide and/or fragment of this invention under conditions whereby an antigen/antibody complex can form and detecting formation of an antigen/antibody complex, thereby detecting the presence of a *Chlamydia* antibody of this invention in the sample.

The sample of this invention can be any sample in which a *Chlamydia* protein can be present. For example, the sample can be a body fluid, cells or tissue that can contain a *Chlamydia* protein, including but not limited to, vaginal fluid, vaginal tissue, vaginal washing, vaginal swab, urethral swab, urine, blood, serum, plasma, saliva, semen, urethral discharge, vaginal discharge, sputum, bronchoalveolar lavage, joint fluid, cerebrospinal fluid and cells, fluids and/or tissue from any organs to which a *Chlamydia* protein can disseminate, including lung, liver, heart, brain, kidney, spleen, muscle, etc., and any combination thereof.

Furthermore the sample may consist of cells and/or fluid from any site of infection, including but not limited to the cervical canal, uterus, fallopian tubes, testes, anus, throat, lungs, skin, eyes, gastro-intestinal tract, or body cavity. These samples can be used fresh, or stored (frozen, dried, refrigerated, as appropriate) for later use. The samples can be used in their native form (urine), or processed, extracted, solubilized, or manipulated. Any *Chlamydia* in these samples can be either viable or dead, whole cell or disrupted, processed or unprocessed.

Additionally, the present invention provides a method of diagnosing *Chlamydia* infection in a subject, comprising contacting a biological sample from the subject with a polypeptide and/or fragment of this invention under conditions whereby an antigen/antibody complex can form; and detecting formation of an antigen/antibody complex, thereby diagnosing *Chlamydia* infection in the subject.

A method of diagnosing *Chlamydia* infection in a subject is further provided, comprising contacting a biological sample from the subject with an antibody of this invention under conditions whereby an antigen/antibody complex can form; and detecting formation of an antigen/antibody complex, thereby diagnosing *Chlamydia* infection in the subject.

As set forth herein, the term "immunogenic fragment" means a fragment (e.g., a peptide) of a protein that can stimulate either humoral or cellular immune responses in the subject. An immunogenic fragment of this invention can comprise, consist essentially of and/or consist of one, two, three, four or more epitopes of a protein of this invention. An immunogenic fragment can be any fragment of contiguous amino acids of a protein of this invention and can be for example, 5, 10, 15, 20, 25, 30, 35, 40, 45, 50, 75, 80, 85, 90, 95, 100, 125, 150, 175, 200, 250, 300, 350, 400, 450, 500, 550, 600 or more amino acids in length, including any number between or beyond those numbers recited herein (e.g., 23, 47 or 468 amino acids). Identification of any such immunogenic fragments is routine in the art.

An immune response elicited or produced by carrying out the methods of this invention employing a protein and/or immunogenic fragment thereof can be a protective immune response, a cellular immune response, a humoral immune response, a Th1 immune response, a Th2 immune response and any combination thereof.

To stimulate the humoral arm of the immune system, i.e., the production of antigen-specific antibodies, an immunogenic fragment can include at least about 5-10 contiguous amino acid residues of the full-length molecule, or at least about 15-25 contiguous amino acid residues of the full-length molecule, or at least about 20-50 or more contiguous amino acid residues of the full-length molecule, that define one or more (e.g., 2, 3, 4, 5, 6, etc.) epitopes, or any integer between five amino acids and the full-length sequence, provided that the fragment in question retains immunogenic activity, as measured by any art-known assay, such as, e.g., the ones described herein and/or those known in the art.

Regions of a given polypeptide that include an epitope can be identified using any number of epitope mapping techniques, well known in the art. (See, e.g., *Epitope Mapping Protocols in Methods in Molecular Biology*, Vol. 66, Glenn E. Morris, Ed., 1996, Humana Press, Totowa, N.J.). For example, linear epitopes can be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al. (1984) *Proc. Natl. Acad. Sci.* USA 81:3998-4002; Geysen et al. (1986) *Molec. Immunol.* 23:709-715, all incorporated herein by reference in their entireties.

Similarly, conformational epitopes are readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al., *Proc. Natl. Acad. Sci* USA (1981) 78:3824-3828) for determining antigenicity profiles and the Kyte-Doolittle technique (Kyte et al., *J. Mol. Biol.* (1982) 157:105-132) for hydropathy plots.

Generally, T-cell epitopes that are involved in stimulating the cellular arm of a subject's immune system are short peptides of about 8-25 amino acids, and these are not typically predicted by the above-described methods for identifying humoral epitopes. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenic fragments can also be identified based on their ability to stimulate lymphocyte proliferation in response to stimulation by various fragments from the antigen of interest.

The term "epitope" as used herein refers to at least about 3 to 5, or about 5 to about 10 or about 5 to about 15, and not more than about 1,000 amino acids (or any integer therebetween), which define a sequence that by itself or as part of a larger sequence, binds to an antibody generated in response to such sequence or stimulates a cellular immune response. There is no critical upper limit to the length of the fragment, which can comprise nearly the full-length of the protein sequence, or even a fusion protein comprising two or more epitopes from a single or multiple chlamydial proteins. An epitope for use in the subject invention is not limited to a polypeptide having the exact sequence of the portion of the parent protein from which it is derived. Indeed, there are many known strains or isolates of *Chlamydia* and there are several variable domains that exhibit relatively high degrees of variability between isolates. Thus, the term "epitope" encompasses sequences identical to the native sequence, as well as modifications to the native sequence, such as deletions, additions and substitutions (generally, but not always, conservative in nature).

"Boost" or "booster" means a second immunization, after an initial (or "priming") immunization that enhances the immune response of the subject. Therefore, in some embodiments, the invention provides a composition that produces an anamnestic response against a *Chlamydia* infection, in a sensitized subject, comprising an anamnestic response-inducing amount of a *Chlamydia* protein immunizing component. As used herein, the term "anamnestic response" means a secondary (booster) immune response in a sensitized subject. By "sensitized subject" is meant a subject that has previously been in contact with a chlamydial antigen or antigens, either by natural exposure or by vaccination (primary immunization) with *Chlamydia* protein immunizing components.

The pharmaceutical compositions of this invention include those suitable for oral, rectal, topical, inhalation (e.g., via an aerosol) buccal (e.g., sub-lingual), vaginal, rectal, intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and/or transdermal administration. The compositions herein may also be administered via a skin scarification method, or transdermally via a patch or liquid. The compositions may be delivered subdermally in the form of a biodegradable material that releases the compositions over a period of time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

An adjuvant of this invention, such as, for example, an immunostimulatory cytokine, can be administered before, concurrent with, and/or within a few hours, several hours, and/or 1, 2, 3, 4, 5, 6, 7, 8, 9, and/or 10 days before or after the administration of a composition of this invention to a subject.

Furthermore, any combination of adjuvants, such as immunostimulatory cytokines, can be co-administered to the subject before, after or concurrent with the administration of a composition of this invention. For example, combinations of immunostimulatory cytokines, can consist of two or more immunostimulatory cytokines of this invention, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

Pharmaceutical compositions comprising a composition of this invention and a pharmaceutically acceptable carrier are also provided. The compositions described herein can be formulated for administration in a pharmaceutical carrier in accordance with known techniques. See, e.g., Remington, *The Science and Practice of Pharmacy* (latest edition). In the manufacture of a pharmaceutical composition according to embodiments of the present invention, the composition of this invention is typically admixed with, inter alia, a pharmaceutically acceptable carrier. Consistent with previous descriptions provided herein, by "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

The pharmaceutical compositions of this invention include those suitable for oral, rectal, topical, inhalation (e.g., via an aerosol) buccal (e.g., sub-lingual), vaginal (e.g., vaginal ring), rectal, intraurethral, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration. The compositions herein can also be administered via a skin scarification method or transdermally via a patch, liquid or gel. The compositions can be delivered subdermally in the form of a biodegradable material that releases the compositions over time. The most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

"Effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science and Practice of Pharmacy* (20th ed. 2000)). As a general proposition, a dosage from about 0.01 µg/kg to about 50 mg/kg will have therapeutic efficacy, with all weights being calculated based upon the weight of the composition.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), reduced severity or complications, reduced pathological effects, delay in the progression of the disorder, disease or illness, delay of the onset of the disease, disorder, or illness, and/or change in clinical parameters of the condition, disorder, disease or illness, etc., as would be well known in the art.

By "prevent," "preventing" or "prevention" is meant to avoid or eliminate the development and/or manifestation of a pathological state and/or disease condition or status in a subject.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. In some embodiments, alternate day dosing can be employed (e.g., every other day). The amount and frequency of administration of the composition of this invention will vary depending on the particular condition being treated or to be prevented and the desired therapeutic effect.

In additional embodiments of this invention, the compositions of this invention can comprise a protein and/or immunogenic fragment thereof of a different pathogenic organism in any combination [e.g., a pathogenic organism that is sexually transmitted, including but not limited to: *Trichomonas* (e.g., *Trichomonas vaginalis*); a pathogenic yeast or fungus (e.g., *Candida albicans*), *Neisseria* (e.g., *N. gonorrhea*), *Treponema pallidum*, and pathogenic viruses (e.g., herpes simplex virus (HSV), human immunodeficiency virus (HIV), human papilloma virus (HPV)]. The compositions of the present invention can also comprise a protein and/or immunogenic fragment from other chlamydial species, including but not limited to *Chlamydia muridarium*, *Chlamydia pneumoniae* and *Chlamydia caviae*.

As used herein, "detecting" or "detection" means testing, screening or otherwise determining the presence and/or absence of a *Chlamydia* protein, nucleic acid and/or antibody in a subject. Such detecting or detection can be carried out by methods well known in the art.

As used herein "effective response" or "responding effectively" means a positive or beneficial response to a particular treatment in contrast to a "lack of an effective response" which can be an ineffectual, negative or detrimental response as well as the lack of a positive or beneficial response. An effective response or lack of effective response (i.e., ineffective response) is detected by evaluation, according to known protocols, of various immune functions (e.g., cell-mediated immunity, humoral immune response, etc.) and pharmacological and biological functions as would be known in the art.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example I

Profiling of Human Antibody Responses to *Chlamydia trachomatis* Urogenital Tract Infection Using Microplates Arrayed with 156 Chlamydial Fusion Proteins Chlamydial Infection.

*C. trachomatis* serovar D (provided by Cho-Chou Kuo, University of Washington, Seattle) was used to infect HeLa cells (ATCC, Manassas, Va.) as described elsewhere (Greene et al. *Infect. Immun.* 72:451-460). Infection was allowed to proceed for various periods of time as indicated for individual experiments at a multiplicity of infection of 1 or as indicated for individual experiments. At the end of infection, the culture samples were either fixed and permeabilized for immunofluorescence staining or lysed to produce whole-cell lysates for precipitation or Western blot assays.

Cloning of Chlamydial Genes and Expression of Chlamydial Proteins.

A total of 156 open reading frames (ORFs) were selected from the *C. trachomatis* serovar D genome sequence. These ORFs are distributed across the entire genome, with representatives in every genome sector. Although no particular programs were used to selectively include or exclude any particular gene classes, the 156 ORFs are mainly composed of hypothetical genes. The 156 ORFs from the serovar D genome plus MOMP genes from eight other *C. trachomatis* serovar genomes were cloned into a pGEX vector system (Amersham Biosciences Corp., Piscataway, N.J.). This vector system allows the protein of interest to be expressed as a fusion protein with glutathione S-transferase (GST) fused to the N terminus of the chlamydial protein (Dong et al. (2004) *Mol. Microbiol.* 52:1487-1494; Sharma et al. (2004) *Infect. Immun.* 72:7164-7171; Zhong et al. (2001) *J. Exp. Med* 193: 935-942). Protein expression was induced with isopropyl-β-D-thiogalactoside (IPTG; Invitrogen, Carlsbad, Calif.). To ensure that each fusion protein is produced with adequate quantities of full-length fusion proteins, induction of fusion protein expression was individually optimized using the following variables: IPTG concentration (0.1 to 5 mM), starting number of bacteria (optical density [OD], 0.5 to 1.5), incubation temperature (10° C. to 37° C.), and time (0.5 h to overnight). After protein induction, bacteria were harvested via centrifugation. The bacterial pellets were resuspended in a Triton lysis buffer (1% Triton X-100, 1 mM phenylmethylsulfonyl fluoride, 75 IU/ml of aprotinin, 20 μM leupeptin, and 1.6 μM pepstatin in PBS [phosphate-buffered saline at pH 7.5]) and were lysed by short pulses of sonication on ice. After a high-speed centrifugation to remove debris, bacterial lysates were aliquoted and stored at −80° C. The quality of the expressed fusion proteins was assessed by purifying the fusion proteins from a portion of the lysates using glutathione-conjugated agarose beads (Amersham Biosciences Corp.). The fusion proteins were checked on sodium dodecyl sulfate (SDS)-polyacrylamide gels stained with a Coomassie blue dye (Sigma). Bacterial lysate samples that showed a prominent band at the expected molecular weight position were used for the subsequent microplate array assays.

Arraying Chlamydial Proteins onto Microplates Precoated with Glutathione.

The bacterial lysates containing the fusion proteins were added to glutathione-coated 96-well microplates (Pierce, Rockford, Ill.) at a 1:10 dilution in PBS with a total volume of 200 μl/well. The plates were incubated overnight at 4° C. to allow GST fusion proteins to bind to the glutathione immobilized on the plate. To minimize differences in the quantity of fusion proteins captured on the plates between lysate samples, an excessive amount of each fusion protein was used to saturate the glutathione-coated assay plates. 20 μl bacterial lysate per well was found to be sufficient for saturating the assay plate if the amount of full-length fusion protein precipitated from the 20-μl bacterial lysate was visible on a SDS gel after Coomassie blue staining. After two washes with PBS-0.05% Tween (Sigma) and blocking with 2.5% milk in PBS (2.5 g of nonfat dry milk in 100 ml PBS) at room temperature for 1 h, the plates were ready for use.

Use of Microplates Arrayed with Chlamydial Fusion Proteins to Detect Human Antibodies.

Human sera were collected from women seen in the Project SAFE research clinic in San Antonio, Tex., who had been diagnosed with *C. trachomatis* cervical infections. Women enrolled in this 5-year follow-up study were screened annually for sexually transmitted infections, including chlamydial infection. The diagnosis was based on detection of *C. trachomatis*-specific nucleic acids in endocervical secretions using a ligase chain reaction method without distinguishing the serotypes of the organisms (Abbott LCX; Abbot Laboratories, Chicago, Ill.). The sera were collected at the time of clinic visits and stored in aliquots at −20° C. The human sera used in the current study were from the initial visit. An institutional review board exempt permit is in place for the current study.

A total of eight sera from healthy female individuals without *C. trachomatis* infection were used as negative controls. To minimize the detection of cross-reactive antibodies (human sera may contain antibodies reactive with bacterial antigens that potentially contaminate the microplate wells during the fusion protein array), all serum samples were preabsorbed with bacterial lysates. The bacterial lysates were made in the same way as the fusion protein-containing lysates except that XL1-Blue bacteria transformed with the pGEX-6p-2 vector plasmid alone were used. Note that the bacterial lysates used for preabsorption contain free GST. After preabsorption, both the serum samples from patients and those from healthy individuals were titrated for their ability to recognize chlamydial antigens in an immunofluorescence assay. Although the patient sera displayed high antibody titers (>1:1,000) in recognizing chlamydial antigens, the healthy sera did not show any significant binding to the chlamydial antigens (<1:20). For the microplate array assay, the preabsorbed serum samples were diluted in PBS containing 10% fetal calf serum and applied to the microplates with the bound fusion proteins for 2 h at room temperature. After a wash, alkaline phosphatase-conjugated goat anti-human immunoglobulin G (IgG; Jackson ImmunoResearch Laboratories, Inc., West Grove, Pa.) in combination with the substrate p-nitrophenylphosphate (Sigma) was used to visualize the primary antibody binding. The human antibody binding to chlamydial fusion proteins was quantitated by reading the absorbance (OD) at 405 nm with a microplate reader (Molecular Devices, Ramsey, Minn.). In some assays, the human antibody samples were also preabsorbed with lysates made from either HeLa cells alone or *C. trachomatis* serovar D-infected HeLa cells at 4° C. overnight in addition to the bacterial lysate absorption.

Immunoprecipitation and Western Blotting.

Immunoprecipitation and Western blotting were carried out as described previously (Dong et al. (2004) *Infect. Immun.* 72:3869-3875; Dong et al. (2004) *Infect. Immun.* 72:3863-3868; Su et al. (2004) *J. Biol. Chem.* 279:9409-9416; Zhong et al. (1996) *J. Exp. Med.* 184:2061-2066; Zhong et al. (2001) *J. Exp. Med.* 193:935-942). For immunoprecipitation, human sera were bound to protein G/A agarose beads (Amersham Biosciences Corp.) and the bead complexes were used to precipitate bacterial lysates containing the desired chlamydial fusion proteins or *chlamydia*-infected HeLa cell lysates containing endogenous chlamydial proteins. The precipitates were resolved in a SDS-polyacrylamide gel and transferred to nitrocellulose membranes. The blots were detected with antibodies specific to individual chlamydial proteins (monoclonal antibody 100a to chlamydial protease-like activity factor [CPAF], a mouse antiserum to MOMP, and another mouse antiserum to CT089) as previously described (Dong et al. (2004) *Infect. Immun.* 72:3869-3875; Sharma et al. (2004) *Infect. Immun.* 72:7164-7171; Zhong et al. (2001) *J. Exp. Med.* 193:935-942). The primary antibody binding was detected by a goat anti-mouse IgG conjugated with horseradish peroxidase (Jackson ImmunoResearch Laboratories).

For Western blotting, which was used to confirm the reactivity of human serum antibodies with chlamydial fusion proteins in the present study, the purified chlamydial fusion proteins were resolved in the SDS gel and transferred to nitrocellulose membranes. The preabsorbed human serum samples, after the appropriate dilution as indicated for individual experiments, were applied to the nitrocellulose membranes. Human antibody binding was detected with a goat anti-human IgG conjugated with horseradish peroxidase (Jackson ImmunoResearch Laboratories). A standard enhanced chemiluminescence (ECL) detection system was used to visualize antibody detection (Su et al. (2004) *J. Biol. Chem.* 279:9409-9416).

Immunofluorescence Assay.

*C. trachomatis*-infected HeLa monolayers grown on coverslips for various times as indicated for individual experiments were processed for antibody staining as previously described (Greene et al. *Infect. Immun.* 72:451-460; Xiao et al. (2004) *Infect. Immun.* 72:5470-5474). For monitoring human serum absorption efficiency, human antibody samples that had or had not been absorbed previously with uninfected or *chlamydia*-infected HeLa cell lysates as described above were added to the coverslips. The primary antibody binding was visualized with a Cy2-conjugated goat anti-human IgG. The Hoechst DNA dye (Sigma) was used to visualize both host nuclei and chlamydial inclusions. For localization of endogenous chlamydial antigens, antibodies against individual chlamydial proteins raised in mice with the corresponding chlamydial fusion proteins were used in combination with a rabbit anti-chlamydial heat shock protein as primary antibodies. The reactivities of the two primary antibodies were visualized with Cy3-conjugated goat anti-mouse and Cy2-conjugated goat anti-rabbit antibodies together with the Hoechst dye. Images were acquired under an Olympus (Seattle, Wash.) AX-70 fluorescence microscope using SimplePCI software (Olympus) as previously described (Fan et al. (1998) *J. Exp. Med.* 187:487-496; Sharma et al. (2004) *Infect. Immun.* 72:7164-7171).

Development of a Microplate Assay Using Chlamydial Fusion Proteins.

A total of 156 chlamydial proteins (Table 1) were selected to establish a microplate-based protein array assay. The 156 chlamydial proteins were expressed as GST fusion proteins. The quality of the chlamydial fusion proteins was monitored on a SDS-polyacrylamide gel. As an example, 26 representative fusion proteins induced under a single protein expression condition were examined on a SDS gel stained with Coomassie blue. In most cases, a dominant band migrating at the expected molecular weight was purified from the corresponding bacterial lysates by using glutathione-conjugated agarose beads, indicating that the GST fusion proteins are readily captured from the bacterial lysates by the immobilized glutathione. For the fusion proteins with obvious degradation and/or contaminated bands (GST-CT101, -CT119, -CT141, -CT449, and -CT618), the expression conditions were further optimized so that a dominant full-length band was produced in each of these samples.

To evaluate whether the GST-chlamydia fusion proteins can be recognized by human antibodies generated during natural chlamydial infection, the human antibodies were reacted with protein G/A-agarose beads and the bead complexes were used to precipitate either the bacterial lysates containing the GST-chlamydia fusion proteins or *chlamydia*-infected HeLa cell lysates containing the endogenous chlamydial antigens. The human antibodies precipitated both the recombinant GST-chlamydia fusion proteins and endogenous chlamydial proteins CT089, MOMP and CPAF, suggesting that the fusion proteins can be used to detect human antichlamydial antibodies.

Identification of Immune-Reactive Antigens Recognized by Human Antibodies.

Microplates arrayed with 156 chlamydial fusion proteins were used to measure the reactivities of 15 sera from women urogenitally infected with *C. trachomatis*. The binding of a given human serum to a given fusion protein with an OD four times above the background was determined as positive. Differences in the number of chlamydial fusion proteins recognized by different human serum samples were observed. For example, serum 14 recognized 18 of the 156 chlamydial fusion proteins, while serum 2 recognized only 2. Although each serum displayed a unique reactivity pattern in terms of the types of chlamydial fusion proteins, many of the 15 sera recognized the same fusion proteins. The number of human sera that positively recognized a given fusion protein is defined as the recognition frequency. Chlamydial proteins recognized at a higher frequency are considered to be more immunodominant during chlamydial infection.

Based on the criteria used in previous antigenicity analyses (Getzoff et al. (1988) *Adv. Immunol.* 43:1-98; Geysen et al. (1987) *Science* 235:1184-1190; Zhong et al. (1990) *Infect. Immun.* 58:1450-1455), the chlamydial fusion proteins that were recognized by 8 or more of the 15 human serum samples were considered to be the dominant antigens. Seven out of the 156 chlamydial proteins meet this requirement: CT089 (an LcrE homologue, recognized by 9 human sera), CT147 (a hypothetical protein, recognized by 13 sera), CT226 (a hypothetical protein, recognized by 8 sera), CT681 (MOMP, recognized by 8 sera), CT694 (a hypothetical protein, recognized by 8 sera), CT795 (a hypothetical protein, recognized by 9 sera), and CT858 (CPAF, recognized by 14 sera). Since immunodominance of a given protein is also affected by antibody titers, the titers of antibodies reactive to each chlamydial fusion protein were further compared. The raw ODs measured between each serum antibody and chlamydial fusion protein were used to represent the antibody titers (accumulative ODs from all 15 antibody samples and average ODs). Interestingly, the seven fusion proteins that were recognized by human antibodies with the highest frequency also maintained the highest accumulative and average ODs. The 15 human sera were pooled at an equal ratio and reacted with the 156 fusion proteins. The raw ODs obtained with the pooled human serum samples were similar to the average ODs obtained with the individual samples, indicating that the pooled serum samples can be used to measure the overall reactivity of the individual human sera. As a negative control, sera were pooled from eight healthy individuals without chlamydial infection and the reactivity of the pooled negative serum samples with the chlamydial fusion proteins was similarly measured. No significant reactivity was found (none of the ODs was near or above 0.2). By considering both the recognition frequency and the titer, it was determined that the fusion proteins recognized by >50% of the human antiserum samples with a raw OD significantly above background (with an average OD equal to or above 0.2) were relatively immunodominant antigens under the current assay conditions. The same seven antigens recognized by eight or more human serum samples—CT089 (LcrE), CT147, CT226, CT681 (MOMP), CT694, CT795, and CT858 (CPAF)—also meet the new requirement for immunodominant antigens.

To confirm that the antibody binding to the arrayed fusion proteins is specific to chlamydial antigens, an additional absorption experiment was carried out using the endogenous chlamydial proteins. The pooled patient sera were absorbed with either uninfected or *chlamydia*-infected HeLa cell lysates before the sera were reacted with the fusion proteins arrayed on the plate. The antibody binding to all seven immune-reactive fusion proteins was completely removed by absorption with the *chlamydia*-infected but not the uninfected HeLa cell lysates.

Antigenicity Titration of the Identified Immunodominant Antigens.

The pooled sera from either the 15 patients or the 8 healthy individuals were serially diluted and analyzed against the seven immune-reactive antigens and eight other MOMPs by both a fusion protein array enzyme-linked immunosorbent assay (ELISA) and a Western blot assay. The ODs decreased as the pooled positive serum samples were diluted from 1:100 to 1:12,500, suggesting that the chlamydial protein-specific antibodies were not saturated under these dilutions. The GST-CPAF fusion protein was significantly recognized by the pooled positive sera at a dilution of 1:12,500, CT795 and CT089 at 1:2,500, and CT147, CT226, CT694, and various MOMPs at 1:500, demonstrating that CPAF, CT795, and CT089 are more immunodominant than MOMP regardless of the types of MOMPs analyzed. Comparing the nine MOMPs, higher ODs were obtained with MOMPs from serovars B, Ba, D, E, and L2, all of which belong to the *C. trachomatis* subspecies B complex, suggesting that the 15 patients were predominantly infected with B complex serovars, most likely serovars D and E, in agreement with the epidemiological finding that both serovars D and E are among the most prevalent *C. trachomatis* serotypes in individuals with sexually transmitted chlamydial infections (Bandea et al. (2001) *Sex. Transm. Infect.* 77:419-422; Choi et al. (2001) *J. Korean Med. Sci.* 16:15-19; Lan et al. (1995) *J. Clin. Microbiol.* 33:3194-3197; Lan et al. (1993) *J. Clin. Microbiol.* 31:1060-1065; Singh et al. (2003) *J. Clin. Microbiol.* 41:2700-2702). The GST-alone control was not significantly recognized at any dilution. The pooled negative sera from eight normal individuals displayed a minimal level of reactivity even at a 1:100 dilution. The above results, obtained with varying dilutions of human serum samples, not only confirmed the observations presented regarding identification of immune reactive antigens recognized by human antibodies presented above, more importantly, provided a more detailed analysis of the relative antigenicities of the immunodominant antigens and of the various MOMPs.

A Western blot assay was used to confirm the above observations. The same seven immunodominant fusion proteins, together with eight other MOMPs and several control proteins, were used as antigens. A dominant full-length fusion protein band migrating at the expected molecular weight position was identified for each fusion protein sample. When the antigens were detected on the Western blot, the pooled positive serum samples recognized CPAF at a 1:1,000,000 dilution, CT795 and CT089 at 1:100,000, and the rest of the chlamydial fusion proteins at 1:10,000. The control fusion proteins CT112, CT574, CT606, and GST alone were not detected regardless of the serum dilution. Among the nine MOMPs, the pooled patient sera preferentially recognized MOMPs from the B complex serovars, including B, Ba, D, E, and L2. The pooled negative sera displayed no detectable reactivity with the chlamydial fusion proteins at 1:10,000. These Western blot results were largely consistent with the ELISA data.

Characterization of the Immune-Reactive Antigens.

To evaluate the expression patterns and determine the locations of the endogenous proteins, antibodies were generated against each of the newly identified immune-reactive antigens and used to track the endogenous proteins in *chlamydia*-infected cultures. As a control, MOMP was detected completely overlapping with intravacuolar organisms at both early (8-h) and late (48-h) stages of infection, while CPAF was detected only in the infected-cell cytosol at the late infection stage. The hypothetical protein, CT226, was detected on the inclusion membrane at the late infection stage but was not detectable at the early stage. The hypothetical protein, CT147, was detected during the entire infection course, inside the inclusion at the early infection stage and in the peripheral region of the inclusion at the late stage. The hypothetical protein, CT795, was expressed early and appeared to be restricted to some but not all inclusions, while CT694 was detected only at the late stage of infection within the inclusion (mostly overlapping with chlamydial organisms). Finally, CT089 was detected throughout the infection cycle overlapping with the intravacuolar chlamydial organisms, an expression/localization pattern similar to that of MOMP.

Example II

The Hypothetical Protein CT813 is Localized in the Chlamydia trachomatis Inclusion Membrane and is Immunogenic in Women Urogenitally Infected with C. trachomatis Chlamydial Organisms and Infection.

The chlamydial serovars/strains used for the present study include A, B, C, D, E, F, G, I, K, L1, L3, and Ba (obtained from Harlan Caldwell at the Rocky Mountain Laboratory, NIAID, NIH, Hamilton, Mont.), 6BC (Thomas Hatch at the University of Tennessee, Memphis) (Everett et al. (1991) Infect. Immun. 59:2853-2855), MoPn (Louis De La Maza, University of California, Irvine) (Pal et al. (1996) Infect. Immun. 64:5341-5348), and L2 and GPIC. These organisms were grown, purified, and titrated as previously described (Greene et al. (2004) Infect. Immun. 72:451-460). Aliquots of the organisms were stored at −80° C. until use. HeLa cells (ATCC, Manassas, Va.) maintained in Dulbecco modified Eagle medium (GIBCO BRL, Rockville, Md.) with 10% fetal calf serum (GIBCO BRL) at 37° C. in an incubator supplied with 5% $CO_2$ were used for the present study. To prepare chlamydial infection samples for an immunofluorescence assay, HeLa cells were grown on glass coverslips in 24-well plates overnight prior to chlamydial inoculation. Chlamydial organisms diluted in Dulbecco modified Eagle medium with 10% fetal calf serum and 2 µg/ml of cycloheximide (Sigma, St. Louis, Mo.) were directly inoculated onto the cell monolayers. The infection dose was pretitrated for individual serovars, and an infection rate of ~50% was applied for all serovars. The cell samples were cultured at 37° C. in a $CO_2$ incubator and processed at various time points after infection as indicated for the individual experiments. For the Western blot assay, the chlamydial infection was carried out similarly as described above except that the cell samples were grown in 75-$cm^2$ tissue culture flasks and collected via lysis with a 2% sodium dodecyl sulfate (SDS) sample buffer.

Prokaryotic Expression of Chlamydial Fusion Proteins and Production of Antifusion Protein Antibodies.

The ORFs coding for hypothetical proteins, including the CT813 protein, and various known proteins, including IncG, IncA, MOMP, HSP60, and CPAF from the C. trachomatis serovar D genome, were cloned into pGEX vectors (Amersham Pharmacia Biotech, Inc., Piscataway, N.J.) and expressed as fusion proteins with glutathione S-transferase (GST) fused to the N terminus of the chlamydial proteins. Expression of the fusion proteins was induced with isopropyl-β-D-thiogalactopyranoside (IPTG; Invitrogen, Carlsbad, Calif.), and the fusion proteins were extracted by lysing the bacteria via sonication in Triton X-100 lysis buffer (1% Triton X-100, 1 mM phenylmethylsulfonyl fluoride, 75 units/ml of aprotinin, 20 µM leupeptin, and 1.6 µM pepstatin). After high-speed centrifugation to remove debris, the fusion protein-containing supernatants were either directly used in various assays or further purified using glutathione-conjugated agarose beads (Pharmacia). The bead-bound fusion proteins were also used to deplete antigen-specific antibodies from antiserum samples. For antibody production, the purified fusion proteins were used to immunize mice as described previously (Zhong et al. (1994) Infect. Immun. 62:1576-1583; Zhong and Brunham. (1992) Infect. Immun. 60:3143-3149; Zhong et al. (1997) Proc. Natl. Acad. Sci. USA 94:13856-13861; Zhong et al. (1993) J. Immunol. 151:3728-3736; Zhong et al. (19910 Infect. Immun. 59:1141-1147). After the titers of specific antibody reached 1:2,000 or higher, the mice were sacrificed. The mouse sera were collected and stored in 50% glycerol at −20° C. until use.

Transient Transfection of Mammalian Cells.

The ORF coding for the CT813 protein from the C. trachomatis serovar D genome was cloned into the pDsRed-Monomer-C1 (BD Biosciences Clontech, San Jose, Calif.) and pFLAG-CMV-4 (Sigma, St. Louis, Mo.) mammalian expression vector systems with either a red fluorescence protein (RFP) gene or a FLAG tag coding sequence (24 nucleotides) fused to the 5' end of CT813. The recombinant plasmids were transfected into HeLa cells by using Lipofectamine 2000 transfection reagent following the protocol recommended by the manufacturer (Invitrogen, Carlsbad, Calif.). At various time points after transfection, indicated for the individual experiments, CT813 protein expression was visualized via either the fusion tag RFP or mouse anti-D813 antibody labeling.

Immunofluorescence Staining.

HeLa cells grown on coverslips were fixed with 4% paraformaldehyde dissolved in phosphate-buffered saline for 20 min at room temperature, followed by permeabilization with 0.1% Triton X-100 for an additional 4 min. After being washed and blocked, the cell samples were subjected to various combinations of antibody and chemical staining. Hoechst (blue) (Sigma) was used to visualize nuclear DNA. A rabbit antichlamydial organism antibody (R1L2, raised with C. trachomatis serovar L2 organisms) (data not shown), anti-CT395 antibody (raised with the CT395 fusion protein; the CT395 protein is a GrpE-related chaperonin with >70% amino acid sequence identity among all chlamydial species), or anti-IncG antibody (provided by Ted Hackstadt at the Rocky Mountain Laboratory, NIAID, NIH, Hamilton, Mont.) (Scidmore-Carlson et al. (1999) Mol. Microbiol. 33:753-765), plus a goat anti-rabbit immunoglobulin G (IgG) secondary antibody conjugated with Cy2 (green) (Jackson ImmunoResearch Laboratories, Inc., West Grove, Pa.) was used to visualize chlamydial inclusions or the inclusion membrane. The mouse antibodies against the CT813 protein, IncG, MOMP (monoclonal antibody, clone MC22), and CPAF (monoclonal antibody, clone 100a) plus goat anti-mouse IgG conjugated with Cy3 (red) (Jackson ImmunoResearch) were used to visualize the corresponding antigens. In some cases, the primary antibodies were preabsorbed with either the corresponding or heterologous fusion proteins immobilized onto agarose beads (Pharmacia) prior to the staining of cell samples. The preabsorption approach was carried out by incubating the antibodies with bead-immobilized antigens for 1 h at room temperature or overnight at 4° C., followed by pelleting of the beads. The remaining supernatants were used for immunostaining. For the transfected cell samples, the CT813 protein was visualized either by the fusion tag RFP or by containing with a mouse anti-CT813 antibody. In addition, the transfected cells were also costained with phalloidin conjugated with Alexa 488 (green) (Molecular Probes, Eugene, Oreg.) to visualize F-actin, an anti-α-tubulin antibody (clone B-5-1-2; Sigma) to detect microtubules, and an anti-cytokeratin 8 antibody (clone M20; Sigma) to detect intermediate filaments (IF). The costainings were visualized by goat anti-mouse IgG conjugated with Cy2 (green) (Jackson ImmunoResearch).

Fluorescence and Confocal Microscopy.

After the appropriate immunolabeling, the cell samples were used for image analysis and acquisition with an Olympus AX-70 fluorescence microscope equipped with multiple filter sets (Olympus, Melville, N.Y.) as described previously (Fan et al. (1998) *J. Exp. Med.* 187:487-496; Greene et al. (2004) *Infect. Immun.* 72:451-460; Xiao et al. (2005) *J. Immunol.* 174:1701-1708; Zhong et al. (2001) *J. Exp. Med.* 193:935-942). Briefly, the multicolor-labeled samples were exposed under a given filter set at a time and the single-color images were acquired using a Hamamatsu digital camera. The single-color images were then superimposed with the software SimplePCI to display multiple colors. An Olympus FluoView laser confocal microscope was used to further analyze the costained samples at the UTHSCSA institutional core facility. All microscopic images were processed using the Adobe Photoshop program (Adobe Systems, San Jose, Calif.).

Western Blot Assay.

The Western blot assay was carried out as described elsewhere (Dong et al. (2005) *Infect. Immun.* 73:1861-1864; Dong et al. (2005) *Infect. Immun.* 73:1868-1872; Fan et al. (1998) *J. Exp. Med.* 187:487-496; Sharma et al. (2005) *Infect. Immun.* 73:4414-4419; Zhong et al. (1996) *J. Exp. Med.* 184: 2061-2066). Briefly, the fusion protein, infected whole-cell lysate, or purified chlamydial organism samples were solubilized in 2% SDS sample buffer and loaded to SDS-polyacrylamide gel wells. After electrophoresis, the proteins were transferred to nitrocellulose membranes and the blots were detected with primary antibodies. Primary antibody binding was probed with a horseradish peroxidase-conjugated secondary antibody and visualized with an ECL kit (Santa Cruz Biotechnology, Inc., Santa Cruz, Calif.).

The Western blot assay was used for the following purposes. To determine whether the CT813 protein is associated with the purified chlamydial organisms, the *chlamydia*-infected whole-cell lysate and purified EB samples were compared for their reactivities with the mouse anti-CT813 antibody. To validate the preabsorption efficiency, the mouse anti-CT813 and anti-IncG antibodies were preabsorbed with or without the corresponding or heterologous fusion proteins as described above and then applied to the nitrocellulose membrane. To monitor the time course of CT813 protein expression, the infected HeLa cell samples were harvested at various time points after infection and resolved by SDS-polyacrylamide gel electrophoresis (PAGE). After the cell samples were transferred onto nitrocellulose membranes, the corresponding protein bands were detected with the mouse antibodies recognizing the CT813 protein, MOMP (clone MC22), and host beta-actin (clone Ac-15). To titrate the pooled human sera for reactivity with chlamydial fusion proteins, the purified fusion proteins were loaded at equal amounts to the corresponding lanes of SDS-polyacrylamide gels in multiple sets. One set was stained with brilliant blue R-250 (Sigma) to visualize the total amount of protein in each lane, and the rest of the sets were transferred onto nitrocellulose membrane to assess human antibody binding to the chlamydial fusion proteins after a serial dilution of the sera.

ELISA.

Ten human sera collected from women diagnosed with *C. trachomatis* urogenital infections (positive sera) and eight human sera collected from women without chlamydial infection (negative sera) were used in the current study. These human sera were measured for their reactivity with the CT813 protein and other chlamydial fusion proteins by using an enzyme-linked immunosorbent assay (ELISA) as described elsewhere (Sharma et al. (2004) *Infect. Immun.* 72:7164-7171; Zhong et al. (1993) *J. Immunol.* 151:3728-3736; Zhong and Brunham. (1990) *Infect. Immun.* 58:3438-3441), except that the fusion proteins were immobilized onto 96-well ELISA microplates (Pierce, Rockford, Ill.) via the interactions between GST and glutathione precoated onto the microplates. Briefly, bacterial lysates containing the GST fusion proteins were directly added to the glutathione plates. After the plates were washed to remove excess fusion proteins and blocked with 2.5% nonfat milk (in phosphate-buffered solution), the human serum samples were approximately diluted and added to the antigen-immobilized microplates. Serum antibody binding was detected with horseradish peroxidase-conjugated goat anti-human IgG (Jackson ImmunoResearch Laboratories, Inc., West Grove, Pa.) in combination with the soluble substrate 2,2'-azinobis(3-ethylbenzothiazoline-6-sulfoforic acid) (ABTS) diammonium salt (Sigma) and quantitated by reading the absorbance (optical density [OD]) at 405 nm using a microplate reader (Molecular Devices Corporation, Sunnyvale, Calif.).

Localization of CT813 Protein to *C. trachomatis* Inclusion Membrane.

To search for new inclusion membrane proteins of *C. trachomatis*, antibodies raised with chlamydial fusion proteins were used to localize the corresponding endogenous proteins in *chlamydia*-infected cells in an immunofluorescence assay. After screening ~300 antibodies, it was found that the antibody raised with the CT813 fusion protein appeared to label the inclusion membrane. The anti-CT813 antibody staining pattern is similar to that of the antibody specifically recognizing IncG, a known chlamydial inclusion membrane protein. As controls, the anti-MOMP antibody detected the intrainclusion organisms and anti-CPAF antibody labeled the cytosol of *chlamydia*-infected cells. To more closely compare the staining patterns of anti-D813 and anti-IncG antibodies, the two antibodies were used to costain the same cell samples. Both conventional fluorescence and laser confocal microscopes revealed that the two antibodies costained the inclusion membrane and that the staining overlapped, confirming that anti-CT813 selectively labeled the *C. trachomatis* inclusion membrane. In a Western blot assay, the anti-CT813 and anti-IncG antibodies detected the corresponding endogenous proteins in the infected whole-cell lysates but not the purified EBs while an equivalent amount of MOMP was detected in both samples, supporting the notion that the CT813 protein is localized mainly in the inclusion membrane.

A preabsorption procedure was used to evaluate whether inclusion membrane labeling by the anti-CT813 antibody is specific to the CT813 protein. In this experiment, the anti-CT813 and control anti-IncG antibodies were preabsorbed with or without the corresponding and heterologous fusion proteins, respectively, before being applied to the *chlamydia*-infected cell samples. Both the anti-D813 and anti-IncG antibodies labeled the chlamydial inclusion membrane. Anti-CT813 staining was removed by preabsorption with the GST-CT813 but not GST-IncG fusion proteins, while anti-IncG staining was blocked by GST-IncG but not GST-D813. The efficiency of the preabsorption procedure was further verified in a Western blot assay. The ability of the anti-D813 and anti-IncG antibodies to recognize both the fusion proteins and endogenous proteins was removed by preabsorption with the homologous but not the heterologous fusion proteins, confirming that the preabsorption was both efficient and specific.

Thus, inclusion membrane staining by the anti-CT813 antibody is specific to the CT813 protein.

Expression of CT813 Protein in *Chlamydia*-Infected Cultures.

CT813 protein expression was monitored in cultures over time by both Western blot and immunofluorescence assays. The anti-D813 antibody detected a band corresponding to the endogenous CT813 protein in *chlamydia*-infected but not uninfected cultures 24 h after infection. The lack of detection of the CT813 protein at earlier time points may be due to an insufficient amount of samples loaded since MOMP, a constitutively expressed major outer membrane protein, was also first detected 24 h after infection. The amounts of total cellular protein loaded to the lanes were similar, as indicated by the detection of host beta-actin. The GST-CT813 fusion protein was detected only by the anti-CT813 but not by the anti-MOMP or anti-beta-actin antibodies, validating the antibody binding specificity.

In an immunofluorescence assay, the CT813 protein was detected as early as 12 h after infection and was present in the inclusion membrane throughout the entire infection course. Since the single-cell-based immunofluorescence microscopy assay is known to be sensitive enough to detect other newly synthesized chlamydial proteins as early as 8 h (Belland et al. (2003) *Proc. Natl. Acad. Sci. USA* 100:8478-8483) and since MOMP was visualized at 8 h after infection in the same assay, the failure to detect the CT813 protein at 8 h postinfection suggests that it may not be expressed by *C. trachomatis* at this time point. This conclusion is consistent with the observation that CT813 was not among the immediate-early genes identified by microarray analysis (Belland et al. (2003) *Proc. Natl. Acad. Sci*. USA 100:8478-8483). However, more-extensive, -sensitive, and -careful analyses are required for determining the precise time points at which the CT813 protein is first expressed.

By BLAST sequence searching, homologues of the CT813 protein were found only in strains/serovars of *C. trachomatis* species, including the mouse biovar MoPn. A mouse polyclonal anti-CT813 antibody was used to screen cell cultures infected with multiple chlamydial serovars/strains from four different species. The anti-CT813 antibody labeled the inclusion membrane in cells infected with all *C. trachomatis* human serovars but not other strains. Although DNA sequence analysis determined that the MoPn genome contains a gene (designated Tc0199 [Read et al. (2000) *Nucleic Acids Res.* 28:1397-1406]) homologous to CT813, the anti-CT813 antibody failed to label the MoPn-infected culture. To test whether this failure is due to the lack of TC0199 protein expression by MoPn or the relative low homology (~36% amino acid identity) between TC0199 and the CT813 protein (thus lack of sufficient cross-reactivity), an antibody raised with the CT0199 fusion protein was used to detect the MoPn-infected culture. The anti-CT0199 antibody labeled the inclusion membrane of MoPn-infected cells, demonstrating that the CT0199 protein is not only expressed but also, like its homologue, the CT813 protein from the *C. trachomatis* human biovar, is localized in the inclusion membrane.

Exogenously Expressed CT813 Protein Displayed a Cytoskeleton-Like Structure.

To evaluate how the CT813 protein behaves in HeLa cells in the absence of chlamydial infection, the CT813 protein was expressed as a fusion protein with an RFP fused to its N terminus (designated RFP-CT813). Surprisingly, the RFP-CT813 fusion protein formed fibers in the transfected cells while the overly expressed RFP alone evenly distributed throughout the cells, including the nuclei. The fibrous structure displayed by the RFP-CT813 fusion protein overlapped with anti-CT813 antibody costaining but did not overlap with either F-actin or microtubules. Although the pattern of RFP-CT813 fibers looks like the pattern of IF visualized by costaining cytokeratin 8, the two did not overlap. To confirm the relationship between RFP-CT813 structure and IF, the costained samples were subjected to a confocal microscopy analysis. The RFP-CT813 fibers did not overlap with the intermediate filaments. The RFP-CT813 fibers were designated as a cytoskeleton-like structure, which was observed throughout the transfection period (from 6 to 24 h posttransfection). The cytoskeleton-like structure formed by RFP-CT813 was unlikely caused by the RFP fusion tag, since the RFP tag alone did not form any obvious fibers and the CT813 protein expressed with only an 8-amino-acid FLAG tag by the pFLAG-CMV vector also displayed a similar cytoskeleton-like structure.

CT813 Protein is Both Expressed and Immunogenic During *C. trachomatis* Infection in Humans.

The human antibody responses to the CT813 protein was used to indirectly assess its expression by *chlamydia* in humans. Serum samples from 10 women diagnosed with *C. trachomatis* urogenital infection were each assayed against chlamydial fusion proteins in an ELISA. The titer of human antibodies specific to the CT813 fusion protein was as high as that of human antibodies specific to the MOMP fusion protein. The observation that the titer of anti-CPAF antibody was the highest is consistent with a previous finding (Sharma et al. (2004) *Infect. Immun.* 72:7164-7171). The titers of antibody to both HSP60 and IncA were lower than that to the CT813 protein. No significant background antibody levels were detected against GST alone. This is probably due to the fact that all human serum samples assayed here were preabsorbed with bacterial lysates containing free GST. To confirm the ELISA specificity, the pooled human samples were subjected to preabsorption with HeLa lysates or *chlamydia*-infected cell lysates in addition to bacterial lysates. Human antibody reactivity with the various chlamydial fusion proteins was blocked by preabsorption with *chlamydia*-infected HeLa lysates but not HeLa-alone lysates. Furthermore, sera from eight women without chlamydial infection reacted minimally with these chlamydial fusion proteins. Human antibody reactivity with the CT813 protein was further confirmed in a Western blot assay. The pooled positive sera recognized all fusion proteins, including GST-CT813 but not GST alone, at a dilution of 1:500. As human serum dilution increased, fewer fusion proteins were recognized. However, the positive sera still recognized CT813, MOMP, and CPAF fusion proteins at a dilution of 1:62,500 while the pooled negative sera failed to recognize any antigens even at 1:500. The Western blot assay result largely supported the above ELISA observation.

Example III

Additional Immunodominant Proteins Identified

Identification of 19 additional chlamydial proteins as immunodomininat was made using the methods described in Example I, differing only in the human patient antisera used. These 19 proteins are listed in Table 2.

Example IV

Further Immunodominant Proteins Identified

Identification of 41 additional chlamydial proteins as immunodominant was made using the methods described herein as well as in Li et al. ("Characterization of fifty putative inclusion membrane proteins encoded in the *Chlamydia trachomatis* genome" *Infect. Immun.* 76 (6): 2746-57 (2008), the entire contents of which are incorporated by reference herein). These 41 proteins are listed in Table 3.

Example V

Protection and Pathology Studies on Immunodominant Proteins

Having determined that the proteins described herein are dominantly recognized by antisera from patients infected with *Chlamydia*, further studies were carried out to evaluate whether these proteins can also induce protective immunity against chlamydial challenge infection in mice and/or reduce oviduct pathology (hydrosalpinx). These studies have shown that immunization with the mouse chlamydial species (MoPn) homologues of CT143, pCT03 (pgp3), CT541 & CT866 can induce protection against challenge infection with MoPn organisms in a mouse urogenital tract infection model (Tables 4-6). Additional antigens tested in the present study failed to induce any significant protection (Tables 4-7). Furthermore, most of the antigens tested in the present study showed reduced oviduct pathology (hydrosalpinx) (Tables 4-5). Further studies are underway to analyze additional proteins of this invention.

Balb/c female mice were immunized with the corresponding purified chlamydial antigens plus CpG adjuvant [for intranasal immunization (i.n.) in Table 5 (Expt. 4)] and emulsified in incomplete Freund's adjuvant (IFA) [for intramuscular injection (i.m.) in Tables 4, 6 and 7 (Expts. 3, 5 and 6]. Mice were immunized three times each with 20 to 200 ug of a given antigen with 10 μg of CpG and equal volume of IFA (IFA for i.m. only). Thirty days after the last injection, mice were challenged intravaginally with live MoPn organisms. On different days (D) after infection, vaginal swabs were taken for monitoring the shedding of live organisms. On days 60 to 80 post infection, all mice were sacrificed for visualizing pathologies (visible hydrosalpinx). The live organism recovery yield was expressed as Log 10 IFUs and the hydrosalpinx pathology as incidence and severity scores. Two control groups were included in each experiment, with CpG+GST immunization for negative control and CpG+MoPn EB as positive control.

The foregoing is illustrative of the present invention, and is not to be construed as limiting thereof. The invention is defined by the following claims, with equivalents of the claims to be included therein. All publications, patent applications, patents, patent publications, sequences (nucleotide sequences, single polymorphism nucleotides, amino acid sequences, etc.) identified in the GenBank® database or other sequence databases according to the accession numbers provided herein, and any other references cited herein are incorporated by reference in their entireties for the teachings relevant to the sentence and/or paragraph in which the reference is presented.

TABLE 1

*C. trachomatis* ORFs expressed as GST-*chlamydia* fusion proteins

| ORF no.[a] | *C. trachomatis* gene | ORF no. | *C. trachomatis* gene |
|---|---|---|---|
| 1 | CT001, hypothetical | 79 | CT384, hypothetical |
| 2 | CT005, hypothetical | 80 | CT395, grpE |
| 3 | CT006, hypothetical | 81 | CT396, dnaK |
| 4 | CT011, hypothetical | 82 | CT406, hypothetical |
| 5 | CT018, hypothetical | 83 | CT407, dksA |
| 6 | CT021, hypothetical | 84 | CT421, hypothetical |
| 7 | CT036, hypothetical | 85 | CT422, metalloproteas |
| 8 | CT049, hypothetical | 86 | CT425, hypothetical |
| 9 | CT056, hypothetical | 87 | CT427, hypothetical |
| 10 | CT058, hypothetical | 88 | CT431, clpP |
| 11 | CT085, hypothetical | 89 | CT442, crpA |
| 12 | CT088, sycE | 90 | CT446, euo |
| 13 | CT089, lcrE | 91 | CT449, hypothetical |
| 14 | CT101, hypothetical | 92 | CT457C, yebC |
| 15 | CT110, groEL1 | 93 | CT473, hypothetical |
| 16 | CT111, groES | 94 | CT474, hypothetical |
| 17 | CT112, pepF | 95 | CT482, hypothetical |
| 18 | CT113, clpB | 96 | CT484, hypothetical |
| 19 | CT115, incD | 97 | CT493C, polA |
| 20 | CT116, incE | 98 | CT546, hypothetical |
| 21 | CT117, incF | 99 | CT548, hypothetical |
| 22 | CT118, incG | 100 | CT560, hypothetical |
| 23 | CT119, incA | 101 | CT565, hypothetical |
| 24 | CT133, hypothetical | 102 | CT569, hypothetical |
| 25 | CT134, hypothetical | 103 | CT571N, gspE |
| 26 | CT135, hypothetical | 104 | CT572, gspD |
| 27 | CT141, secA | 105 | CT573, hypothetical |
| 28 | CT147, hypothetical | 106 | CT574, pepP |
| 29 | CT149, hydrolase? | 107 | CT576, lcrH |
| 30 | CT151, hypothetical | 108 | CT577, hypothetical |
| 31 | CT153, hypothetical | 109 | CT604, groEL2 |
| 32 | CT154, hypothetical | 110 | CT606, hypothetical |
| 33 | CT155, hypothetical | 111 | CT611, hypothetical |
| 34 | CT161, hypothetical | 112 | CT618, hypothetical |
| 35 | CT162, hypothetical | 113 | CT627, yceA |
| 36 | CT163, hypothetical | 114 | CT638, hypothetical |
| 37 | CT164, hypothetical | 115 | CT647, hypothetical |
| 38 | CT165, hypothetical | 116 | CT648, hypothetical |
| 39 | CT171, trpA | 117 | CT654, hypothetical |
| 40 | CT173, hypothetical | 118 | CT657, hypothetical |
| 41 | CT174, hypothetical | 119 | CT659, hypothetical |
| 42 | CT181, hypothetical | 120 | CT668, hypothetical |
| 43 | CT191, hypothetical | 121 | CT670, hypothetical |
| 44 | CT192, hypothetical | 122 | CT671, hypothetical |
| 45 | CT195, hypothetical | 123 | CT676, hypothetical |
| 46 | CT196, hypothetical | 124 | CT681, ompA |
| 47 | CT214, hypothetical | 125 | CT694, hypothetical |
| 48 | CT223, inc | 126 | CT700, hypothetical |
| 49 | CT224, hypothetical | 127 | CT701, secA2 |
| 50 | CT225, hypothetical | 128 | CT705, clpX |
| 51 | CT226, hypothetical | 129 | CT706, clpP2 |
| 52 | CT227C, hypothetical | 130 | CT712, hypothetical |
| 53 | CT228, hypothetical | 131 | CT717, flil |
| 54 | CT229, inc | 132 | CT718, hypothetical |
| 55 | CT232, incB | 133 | CT724, hypothetical |
| 56 | CT233, incC | 134 | CT728, hypothetical |
| 57 | CT260, hypothetical | 135 | CT733, hypothetical |
| 58 | CT266, hypothetical | 136 | CT734, hypothetical |
| 59 | CT277, hypothetical | 137 | CT739C, ftsK |
| 60 | CT286, clpC | 138 | CT741, hypothetical |
| 61 | CT288, hypothetical | 139 | CT753, hypothetical |
| 62 | CT296, hypothetical | 140 | CT755, groEL3 |
| 63 | CT300, hypothetical | 141 | CT716, hypothetical |
| 64 | CT309, hypothetical | 142 | CT764, hypothetical |
| 65 | CT321, secE | 143 | CT768, hypothetical |
| 66 | CT324, hypothetical | 144 | CT779, hypothetical |
| 67 | CT338, hypothetical | 145 | CT789b, hypothetical |
| 68 | CT341, dnaJ | 146 | CT795, hypothetical |
| 69 | CT343, endopeptidase | 147 | CT814, hypothetical |
| 70 | CT344, lon | 148 | CT814.1, hypothetical |
| 71 | CT345, hypothetical | 149 | CT820, fstY |
| 72 | CT351, hypothetical | 150 | CT823C, htrA |
| 73 | CT357, hypothetical | 151 | CT825C, hypothetical |
| 74 | CT358, hypothetical | 152 | CT845, hypothetical |
| 75 | CT365N, hypothetical | 153 | CT847, hypothetical |
| 76 | CT372, hypothetical | 154 | CT849, hypothetical |
| 77 | CT375, D-aa dehydrogenase[b] | 155 | CT850, hypothetical |
| 78 | CT383, hypothetical | 156 | CT858, cpaf |

TABLE 1-continued

C. trachomatis ORFs expressed as GST-chlamydia fusion proteins

| ORF no.[a] | C. trachomatis gene | ORF no. | C. trachomatis gene |
|---|---|---|---|

[a]Renumbered from 1 to 156 for the convenience of the present study. The suffix N or C after the ORF designation indicates either the N terminus or the C terminus of the ORF expressed as a GST fusion protein.
[b]D-aa, D amino acid.

TABLE 2

Chlamydial proteins identified to be immunodominant using antisera from patients urogenitally infected with C. trachomatis

| | |
|---|---|
| 1 | CT001 (9.8 kDa), 2 membrane domain, *Chlamydia*-specific hypothetical protein |
| 2 | CT017 (48 kDa), signal leader peptide, *Chlamydia*-specific hypothetical protein (basic) |
| 3 | CT088 (16 kDa), sycE scc1, probable chaperone for type III pathway |
| 4 | CT101 (18 kDa), *Chlamydia*-specific hypothetical protein (basic) |
| 5 | CT105 (68 kDa), conserved hypothetical protein |
| 6 | CT142 (31 kDa), *Chlamydia*-specific hypothetical protein |
| 7 | CT143 (31 kDa), *Chlamydia*-specific conserved hypothetical protein |
| 8 | CT214 (59 kDa), *Chlamydia trachomatis*-specific hypothetical protein (basic) |
| 9 | CT240 (22 kDa), recR, Recombination/repair protein |
| 10 | CT241 (89 kDa), probable outer membrane protein (Omp85 analog) |
| 11 | CT268 (29 kDa), amiA, probable N-acetylmuramoyl-1-alanine amidase |
| 12 | CT381 (29 kDa), artJ, ABC transporter, probable solute binding protein; possible arginine-binding periplasmic protein 2. |
| 13 | CT456 (102 kDa), Tarp, conserved hypothetical protein (acidic) (related to outer membrane proteins) |
| 14 | CT480 (80 kDa), dppA, ABC transporter solute binding protein; oligopeptide transport system |
| 15 | CT541 (27 Kda), mip, FkbP-type peptidyl-prolyl cis-trans isomerase (MIP-like protein) |
| 16 | CT557 (49 kda), lpdA, pyruvate dehydrogenase E3 component (dihydrolipoamide dehydrogenase) |
| 17 | CT622 (69 kda), conserved hypothetical protein (acidic) |
| 18 | CT866 (85 kDa), glgB, 1,4-alpha-glucan branching enzyme |
| 19 | CT875 (66 kDa), hypothetical protein |

TABLE 3

Chlamydial proteins identified to be immunodominant using antisera from humans infected with C. trachomatis and antisera from animals immunized against C. trachomatis organisms.

| | |
|---|---|
| 1 | CT005 *Chlamydia*-specific conserved hypothetical protein |
| 2 | CT019 (ileS) |
| 3 | CT022 (rl31) |
| 4 | CT046 (hctB) |
| 5 | CT067 (adhesin) |
| 6 | CT099 (trxB) |
| 7 | CT111 (groES) |
| 8 | CT116 (hypothetical protein, Inc?) |
| 9 | CT118 (hypothetical protein IncG) |
| 10 | CT149 (conserved hypothetical protein) |
| 11 | CT153 (*Chlamydia*-specific hypothetical protein) |
| 12 | CT208 (gseA) |
| 13 | CT225 (hypothetical protein) |
| 14 | CT228 (*Chlamydia*-specific conserved hypothetical protein) |
| 15 | CT236 (acpP) |
| 16 | CT237 (fabG) |
| 17 | CT242 (probable outer membrane protein) |
| 18 | CT260 (*Chlamydia*-specific hypothetical protein) |
| 19 | CT278 (nqr2) |
| 20 | CT322 (tufA) |
| 21 | CT328 (tpiA) |
| 22 | CT376 (mdhC) |
| 23 | CT396 (dnaK) |
| 24 | CT414 (pmpC) |
| 25 | CT431 (clpP) |
| 26 | CT450 (yaeS) |
| 27 | CT457 (conserved hypothetical protein, YEBC-related) |
| 28 | CT494 (sohB) |
| 29 | CT507 (rpoA) |
| 30 | CT532 (fabZ) |
| 31 | CT542 (asps) |
| 32 | CT556 (*Chlamydia*-specific hypothetical protein, acidic) |
| 33 | CT578 (*Chlamydia*-specific hypothetical protein) |
| 34 | CT673 (pkn5) |
| 35 | CT733 (*Chlamydia*-specific hypothetical protein, basic)) |
| 36 | CT743 (hctA) |
| 37 | CT759 (conserved hypothetical protein, probably cell wall-binding protein, basic) |
| 38 | CT791 (uvrC) |
| 39 | CT798 (glgA) |
| 40 | CT828 (nrdB) |
| 41 | CT868 (conserved hypothetical protein, possible thiol protease) |

TABLE 4

VacExp3-Balb/c, IM

| | | IFU(Log 10) | | | | | | | | | Oviduct Pathology Hydrosalpinx | | | |
|---|---|---|---|---|---|---|---|---|---|---|---|---|---|---|
| | | | | | | | | | | | Incidence | | | Severity |
| | | D3 | D8 | D13 | D16 | D19 | D22 | D25 | D28 | D31 | Uni- | Bi- | Total | Score |
| CI + GST | X | 5.82 | 5.03 | 3.73 | 3.38 | 1.82 | 0.93 | 0 | 0 | 0 | 1/5 | 2/5 | 3/5 | 4 |
| | SD | 0.46 | 0.41 | 1.49 | 2.23 | 2.51 | 0.99 | 0 | 0 | 0 | | | | 4 |
| CI + MoPnEB | X | 4.00 | 3.10 | 0 | 0 | 0 | 0 | 0 | 0 | 0 | 1/5 | 2/5 | 3/5 | 1.4 |
| | SD | 1.32 | 1.82 | 0 | 0 | 0 | 0 | 0 | 0 | 0 | | | | 1.67 |
| CI + TC0420(CT143) | X | 5.95 | 5.01 | 4.86 | 4.09 | 2.45 | 0 | 0 | 0 | 0 | 1/4 | 2/4 | 3/4 | 3.5 |
| | SD | 0.30 | 0.12 | 0.42 | 1.40 | 1.87 | 0 | 0 | 0 | 0 | | | | 3.42 |
| CI + TC0511(CT240) | X | 5.83 | 5.25 | 4.49 | 4.09 | 3.00 | 0.90 | 0 | 0 | 0 | 0 | 4/5 | 4/5 | 4.2 |
| | SD | 0.30 | 0.48 | 0.65 | 0.77 | 1.43 | 0.91 | 0 | 0 | 0 | | | | 2.77 |
| CI + TC0431(CT153) | X | 5.59 | 4.93 | 4.67 | 4.23 | 3.39 | 1.06 | 0 | 0 | 0 | 3/5 | 1/5 | 4/5 | 2.8 |
| | SD | 0.35 | 0.48 | 0.65 | 0.77 | 1.43 | 0.91 | 0 | 0 | 0 | | | | 3.27 |
| CI + TC0140(CT759) | X | 5.76 | 5.14 | 4.87 | 4.47 | 2.33 | 1.47 | 0.93 | 0.45 | 0 | 1/5 | 3/5 | 4/5 | 4.2 |
| | SD | 0.23 | 0.24 | 0.51 | 1.60 | 2.05 | 2.27 | 2.07 | 1.00 | 0 | | | | 2.86 |

TABLE 4-continued

VacExp3-Balb/c, IM

| | | IFU(Log 10) | | | | | | | | Oviduct Pathology Hydrosalpinx | | | |
|---|---|---|---|---|---|---|---|---|---|---|---|---|---|
| | | | | | | | | | | Incidence | | | Severity |
| | | D3 | D8 | D13 | D16 | D19 | D22 | D25 | D28 | D31 | Uni- | Bi- | Total | Score |
| CT + TC0828(CT541) | X | 5.50 | 4.11 | 3.57 | 2.42 | 1.47 | 0.32 | 0.34 | 0 | 0 | 3/5 | 1/5 | 4/5 | 2.2 |
| | SD | 0.17 | 1.89 | 1.52 | 2.19 | 2.02 | 0.61 | 0.77 | 0 | 0 | | | | 3.27 |

Note:
CI = CpG + IFA
X = mean
SD = standard deviations
Hydrosalpinx severity score
0 = no hydrosalpinx
1 = Hydrosalpinx is only visible after amplification
2 = hydrosalpinx is clearly visible with naked eye but the size is smaller than that of the ovary
3 = similar to ovary
4 = larger than ovary

TABLE 5

VacExp4-Balb/c, IN

| | | IFU(Log 10) | | | | | | | | | Oviduct Pathology Hydrosalpinx | | | |
|---|---|---|---|---|---|---|---|---|---|---|---|---|---|---|
| | | | | | | | | | | | Incidence | | | Severity |
| | | D3 | D8 | D13 | D16 | D19 | D22 | D25 | D28 | D31 | Uni- | Bi- | Total | Score |
| CpG | X | 5.35 | 5.67 | 5.11 | 3.62 | 2.14 | 1.28 | 0.24 | 0 | 0 | 1/5 | 4/5 | 5/5 | 5 |
| | SD | 0.79 | 0.26 | 0.15 | 1.45 | 2.12 | 1.29 | 0.53 | 0 | 0 | | | | 2 |
| CpG + live MoPn EB (50 IFU) | X | 4.07 | 0 | 0 | 0 | 0 | 0 | 0 | 0 | 0 | 0/5 | 1/5 | 1/5 | 0.4 |
| | SD | 0.40 | 0 | 0 | 0 | 0 | 0 | 0 | 0 | 0 | | | | 0.89 |
| CpG + TC0499 (D228) | X | 5.71 | 5.85 | 5.34 | 5.43 | 3.40 | 0.59 | 0.13 | 0 | 0 | 0 | 2/3 | 2/3 | 3.33 |
| | SD | 0.46 | 0.46 | 0.52 | 0.57 | 1.63 | 1.02 | 0.23 | 0 | 0 | | | | 4.16 |
| CpG + TC0846 (D557) | X | 5.32 | 5.86 | 5.38 | 4.38 | 3.39 | 1.86 | 0.25 | 0.10 | 0 | 0 | 4/4 | 4/4 | 3.5 |
| | SD | 0.20 | 0.40 | 0.42 | 1.34 | 2.34 | 2.15 | 0.50 | 0.20 | 0 | | | | 1.91 |
| CpG + pMoPn03 (pCT03) | X | 5.52 | 5.60 | 3.05 | 1.83 | 0.44 | 0 | 0 | 0 | 0 | 1/5 | 1/5 | 2/5 | 1.2 |
| | SD | 0.46 | 0.21 | 2.81 | 2.10 | 0.60 | 0 | 0 | 0 | 0 | | | | 1.60 |

Note:
Hydrosalpinx severity score
0 = no hydrosalpinx
1 = Hydrosalpinx is only visible after amplification
2 = hydrosalpinx is clearly visible with naked eye but the size is smaller than that of the ovary
3 = similar to ovary
4 = larger than ovary

TABLE 6

VacExp5-Balb/c, IM

| | | IFU(Log 10) | | | | | |
|---|---|---|---|---|---|---|---|
| | | D3 | D7 | D14 | D21 | D24 | D27 |
| CI + GST | X | 5.57 | 5.32 | 4.03 | 0.37 | 0.15 | 0 |
| | SD | 0.22 | 0.38 | 1.26 | 0.83 | 0.47 | 0 |
| CI + MoPnEB | X | 5.04 | 3.99 | 1.5503 | 0 | 0 | 0 |
| | SD | 0.63 | 1.01 | 1.5979 | 0 | 0 | 0 |
| CI + CPAF-WT-His(CT858) | X | 5.29 | 5.03 | 2.98 | 0 | 0 | 0 |
| | SD | 0.27 | 0.66 | 1.72 | 0 | 0 | 0 |
| CI + TC0828(CT541) WT | X | 5.58 | 5.36 | 2.77 | 0 | 0 | 0 |
| | SD | 0.12 | 0.24 | 2.06 | 0 | 0 | 0 |
| CI + TC0210(CT823) S247A | X | 4.93 | 5.42 | 4.63 | 0.59 | 0 | 0 |
| | SD | 0.84 | 0.22 | 0.45 | 1.32 | 0 | 0 |
| CI + TC0486(CT214) | X | 5.29 | 5.31 | 3.85 | 1.70 | 0 | 0 |
| | SD | 0.43 | 0.16 | 1.74 | 1.64 | 0 | 0 |
| CI + TC0257(CT866) | X | 5.25 | 5.35 | 3.54 | 0 | 0 | 0 |
| | SD | 0.30 | 0.37 | 2.18 | 0 | 0 | 0 |
| CI + TC0426(CT149) | X | 4.90 | 4.28 | 2.95 | 0.67 | 0 | 0 |
| | SD | 1.15 | 0.93 | 1.99 | 1.18 | 0 | 0 |
| CI + TC0291(CT022) | X | 4.50 | 5.01 | 3.94 | 2.04 | 0 | 0 |
| | SD | 2.02 | 0.89 | 2.21 | 2.05 | 0 | 0 |

Note:
CI = CpG + IFA
X = mean
SD = standard deviations

TABLE 7

VacExp6-Balb/c, IM

| | | IFU(Log 10) | | | |
|---|---|---|---|---|---|
| | | D7 | D14 | D21 | D28 |
| CI + GST | X | 5.69 | 4.33 | 1.71 | |
| | SD | 0.19 | 1.38 | 2.34 | |
| CI + MoPnEB | X | 5.26 | 0 | 0 | |
| | SD | 0.18 | 0 | 0 | |
| CI + TC0273(D005) | X | 5.63 | 5.03 | 0.46 | |
| | SD | 0.17 | 0.80 | 1.02 | |
| CI + TC0387(D111) | X | 5.73 | 4.11 | 0.57 | |
| | SD | 0.15 | 2.31 | 1.27 | |
| CI + TC0480(D208) | X | 5.75 | 4.38 | 1.58 | |
| | SD | 0.16 | 2.45 | 1.56 | |
| CI + TC00675(D396) | X | 5.77 | 4.42 | 0.36 | |
| | SD | 0.13 | 0.94 | 0.41 | |
| CI + TC0794(D507) | X | 5.64 | 4.02 | 0.90 | |
| | SD | 0.18 | 2.47 | 2.00 | |

Note:
CI = CpG + IFA
X = mean
SD = standard deviations

What is claimed is:

1. A method of detecting an antibody to a *Chlamydia* protein in a sample, comprising:
   a) contacting the sample with one or more than one isolated *Chlamydia trachomatis* protein, said one or more than one isolated *Chlamydia trachomatis* protein being detectably labeled and/or immobilized on a solid support, selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, an immunogenic fragment of any of (1)-(12), (15)-(19), (21)-(24) or (27)-(41), and any combination thereof, under conditions whereby an antigen/antibody complex can form; and
   b) detecting antigen/antibody complex formation, thereby detecting an antibody to the *Chlamydia* protein in the sample.

2. The method of claim 1, in addition to contacting the sample with one or more than one isolated *Chlamydia trachomatis* protein of claim 1, further comprising contacting the sample with an isolated *Chlamydia trachomatis* protein selected from the group consisting of (42) CT110 (HSP60), (43) CT119 (IncA), (44) CT858 (CPAF), (45) CT681 (MOMP), an immunogenic fragment of any of (42)-(45), and any combination thereof.

3. The method of claim 1, in addition to contacting the sample with one or more than one isolated *Chlamydia trachomatis* protein of claim 1, further comprising contacting the sample with one or more than one isolated *Chlamydia trachomatis* protein selected from the group consisting of CT001, CT006, CT011, CT018, CT021, CT036, CT049, CT056, CT058, CT085, CT088, CT089, CT101, CT110, CT112, CT113, CT115, CT117, CT119, CT133, CT134, CT135, CT141, CT147, CT149, CT151, CT153, CT154, CT155, CT161, CT162, CT163, CT164, CT165, CT171, CT173, CT174, CT181, CT191, CT192, CT195, CT196, CT214, CT223, CT224, CT226, CT227C, CT229, CT232, CT233, CT266, CT277, CT286, CT288, CT296, CT300, CT309, CT321, CT324, CT338, CT341, CT343, CT344, CT345, CT351, CT357, CT358, CT365N, CT372, CT375, CT383, CT017, CT105, CT142, CT143, CT240, CT241, CT268, CT381, CT456, CT480, CT541, CT557, CT622, CT866, CT875, an immunogenic fragment thereof, and any combination thereof.

4. The method of claim 1, wherein the sample is selected from the group consisting of vaginal fluid, vaginal tissue, vaginal washing, vaginal swab, urethral swab, urine, blood, serum, plasma, saliva, semen, urethral discharge, vaginal discharge and any combination thereof.

5. A method of diagnosing a *Chlamydia* infection in a subject, comprising:
   a) contacting a sample from the subject with one or more than one isolated *Chlamydia trachomatis* protein, said one or more than one isolated *Chlamydia trachomatis* protein being detectably labeled and/or immobilized on a solid support, selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, an immunogenic fragment of any of (1)-(12), (15)-(19), (21)-(24) or (27)-(41), and any combination thereof under conditions whereby an antigen/antibody complex can form; and
   b) detecting antigen/antibody complex formation, thereby detecting an antibody to a *Chlamydia* protein in the sample, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, and thereby diagnosing a *Chlamydia* infection in the subject.

6. A method of detecting a *Chlamydia* protein in a sample, comprising:
   a) contacting the sample with an antibody that specifically binds a *Chlamydia* protein or immunogenic fragment thereof, said antibody that specifically binds a *Chlamydia* protein or immunogenic fragment thereof being detectably labeled and/or immobilized on a solid support, wherein the *Chlamydia* protein is selected from the group consisting of (1) CT828, (2) CT099, (3) CT322, (4) CT457, (5) CY005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, under conditions whereby an antigen/antibody complex can form; and
   b) detecting antigen/antibody complex formation, thereby detecting the *Chlamydia* protein in the sample.

7. A method of diagnosing a *Chlamydia* infection in a subject, comprising:
   a) contacting a sample from the subject with an antibody that specifically binds a *Chlamydia* protein or immunogenic fragment thereof, said antibody that specifically binds a *Chlamydia* protein or immunogenic fragment thereof being detectably labeled and/or immobilized on a solid support, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, under conditions whereby an antigen/antibody complex can form; and
   b) detecting antigen/antibody complex formation, thereby detecting a *Chlamydia* protein, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, and thereby diagnosing a *Chlamydia* infection in the subject.

8. A method of eliciting an immune response to a *Chlamydia* protein in a subject, comprising: administering to the subject an effective amount of a *Chlamydia* protein or an immunogenic fragment thereof, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798, (41) CT868, and any combination thereof, thereby eliciting an immune response to the *Chlamydia* protein in the subject.

9. The method of claim 8, further comprising administering to the subject an adjuvant and/or an immunostimulant.

10. The method of claim 9, wherein the adjuvant and/or immunostimulant is selected from the group consisting of CpG, IL-12 and any combination thereof.

11. The method of claim 8, further comprising administering to the subject a protein or immunogenic fragment thereof of a pathogenic organism other than *Chlamydia trachomatis*.

12. The method of claim 11, wherein the pathogenic organism is selected from the group consisting of *Chlamydia muridarium*, *Chlamydia pneumoniae*, *Chlamydia caviae*, *Trichomonas vaginalis*, *Candida albicans*, *Neisseria gonorrheae*, *Treponema pallidum*, *Herpes simplex* virus, human papilloma virus and human immunodeficiency virus.

13. The method of claim 8, wherein the subject is a human.

14. A method of treating an infection by *Chlamydia* in a subject or preventing a disease or disorder caused by an infection by *Chlamydia* in a subject, comprising administering to the subject an effective amount of an isolated *Chlamydia* protein or immunogenic fragment thereof, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, thereby treating an infection by *Chlamydia* in a subject or preventing a disease or disorder caused by an infection by *Chlamydia* in the subject.

15. The method of claim 14, wherein the subject is a human.

16. A method of reducing the likelihood of infertility due to *Chlamydia* infection in a subject, comprising administering to the subject an effective amount of an isolated *Chlamydia* protein or immunogenic fragment thereof, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, thereby reducing the likelihood of infertility due to *Chlamydia* infection in the subject.

17. The method of claim 16, wherein the subject is a human.

18. A method of reducing the incidence of hydrosalpinx due to *Chlamydia* infection in a subject, comprising administering to the subject a composition comprising an effective amount of an isolated *Chlamydia* protein or immunogenic fragment thereof, wherein the *Chlamydia* protein is selected from the group consisting of (1) CT828, (2) CT099, (3) CT322, (4) CT457, (5) CT005, (6) CT019, (7) CT022, (8) CT046, (9) CT067, (10) CT111, (11) CT116, (12) CT118, (15) CT208, (16) CT225, (17) CT228, (18) CT236, (19) CT237, (21) CT260, (22) CT278, (23) CT328, (24) CT376, (27) CT431, (28) CT450, (29) CT494, (30) CT507, (31) CT532, (32) CT542, (33) CT556, (34) CT578, (35) CT673, (36) CT733, (37) CT743, (38) CT759, (39) CT791, (40) CT798 and (41) CT868, thereby reducing the incidence of hydrosalpinx due to *Chlamydia* infection in the subject.

* * * * *

UNITED STATES PATENT AND TRADEMARK OFFICE
CERTIFICATE OF CORRECTION

PATENT NO. : 9,068,007 B2  
APPLICATION NO. : 13/123407  
DATED : June 30, 2015  
INVENTOR(S) : Zhong It is certified that error appears in the above-identified patent and that said Letters Patent is hereby corrected as shown below:

In the Specification:
Column 3, Line 50: Please correct "CT 111," to read -- CT111, --
Column 3, Line 51: Please correct "CT 116, (9) CT 118, (10)"
   to read -- CT116, (9) CT118, (10) --
Column 4, Line 24: Please correct "of (o)-(n),"
   to read -- of (a)-(n), --

In the Claims:
Column 43, Claim 7, Line 25: Please correct "CTII8,"
   to read -- CT118, --

Signed and Sealed this
Twelfth Day of April, 2016

Michelle K. Lee
*Director of the United States Patent and Trademark Office*